US012138131B2

(12) United States Patent
Fares et al.

(10) Patent No.: US 12,138,131 B2
(45) Date of Patent: Nov. 12, 2024

(54) TOOTH PREPARATION SYSTEM WITH LATERAL PRONGS FOR LIMITING THREE-DIMENSIONAL MOVEMENT

(71) Applicant: Viax Dental Technologies LLC, Miami, FL (US)

(72) Inventors: Mohamed Fares, Beveren (BE); Renan Julian, Aventura, FL (US); Jesse Madsen, Mt. Pleasant, UT (US)

(73) Assignee: Viax Dental Technologies LLC, Miami, FL (US)

( * ) Notice: Subject to any disclaimer, the term of this patent is extended or adjusted under 35 U.S.C. 154(b) by 553 days.

(21) Appl. No.: 17/420,541

(22) PCT Filed: Jan. 6, 2020

(86) PCT No.: PCT/US2020/012357
§ 371 (c)(1),
(2) Date: Jul. 2, 2021

(87) PCT Pub. No.: WO2020/142767
PCT Pub. Date: Jul. 9, 2020

(65) Prior Publication Data
US 2022/0071736 A1    Mar. 10, 2022

Related U.S. Application Data

(60) Provisional application No. 62/874,728, filed on Jul. 16, 2019, provisional application No. 62/788,318, filed on Jan. 4, 2019.

(51) Int. Cl.
*A61C 1/08* (2006.01)
*A61C 1/14* (2006.01)

(52) U.S. Cl.
CPC .............. *A61C 1/082* (2013.01); *A61C 1/14* (2013.01)

(58) Field of Classification Search
CPC ......... A61C 1/082; A61C 1/084; A61C 1/085; A61C 1/14; A61B 17/1617; A61B 17/162;
(Continued)

(56) References Cited

U.S. PATENT DOCUMENTS 472,004 A    3/1892 Parker
1,407,840 A    2/1922 Cruttenden
(Continued)

FOREIGN PATENT DOCUMENTS

CN    104699865 A    6/2015
DE    3730055 A1    3/1989
(Continued)

OTHER PUBLICATIONS

International Search Report including the Written Opinion from Application No. PCT/US2020/012357 mailed May 7, 2020, 21 pages.
(Continued)

*Primary Examiner* — Jacqueline T Johanas
*Assistant Examiner* — Drew S Folgmann
(74) *Attorney, Agent, or Firm* — Lerner David LLP

(57) ABSTRACT

A tooth preparation system (100) includes a dental tool (150) and guide device (110) for contacting the dental tool to limit its movement in removing predetermined tooth structure from a working tooth. The guide device includes a body (120) having an inner surface (146A), a channel (122A, 122B), an aperture (124, 126, 136), and an opening (127A, 127B). The inner surface is configured for attachment to a tooth to releasably fix the guide device. The channel extends partially through the body, defines a longitudinal axis, is configured for contacting a flange (152A, 152B, 154A, 154B) extending from a shaft of the dental tool to limit a movement of the tool, and defines a channel diameter (Continued)

perpendicular to a direction the longitudinal axis extends. The aperture extends through the body and is configured to expose the predetermined tooth structure. The opening extends between the channel and the aperture and has an opening diameter less than the channel diameter.

13 Claims, 14 Drawing Sheets

(58) Field of Classification Search
CPC ............ A61B 17/1633; A61B 17/1642; A61B 17/1673; A61B 17/17; A61B 17/176; B23C 2220/40; B23C 2220/36; B23C 2210/56; Y10T 409/30644; Y10T 409/4077; Y10T 409/4063; B23Q 9/0014
See application file for complete search history.

(56) References Cited

U.S. PATENT DOCUMENTS

| | | | |
|---|---|---|---|
| 2,591,183 | A | 4/1952 | Mintz |
| 2,621,408 | A | 12/1952 | Klein |
| 3,011,259 | A | 12/1961 | Baum |
| 3,063,149 | A | 11/1962 | Suga |
| 3,254,413 | A | 6/1966 | Suga |
| 3,813,777 | A | 6/1974 | Van Handel et al. |
| 4,778,387 | A | 10/1988 | Komatsu |
| 5,575,656 | A | 11/1996 | Hajjar |
| 5,641,287 | A | 6/1997 | Gittleman |
| 5,775,900 | A | 7/1998 | Ginsburg et al. |
| 5,800,168 | A | 9/1998 | Cascione et al. |
| 5,833,693 | A | 11/1998 | Abrahami |
| 5,975,893 | A | 11/1999 | Chishti et al. |
| 6,511,323 | B1 | 1/2003 | Wilkinson |
| 6,537,067 | B1 | 3/2003 | Wennemann |
| 7,004,757 | B2 | 2/2006 | Wilkinson |
| 7,172,424 | B2 | 2/2007 | Wu |
| 7,217,131 | B2 | 5/2007 | Vuillemot |
| 7,393,211 | B2 | 7/2008 | Wilkinson |
| 7,536,234 | B2 | 5/2009 | Kopelman et al. |
| 7,905,726 | B2 | 3/2011 | Stumpel |
| 8,640,338 | B2 | 2/2014 | Jacquemyns |
| 8,651,860 | B2 | 2/2014 | Kwon |
| 8,696,356 | B2 | 4/2014 | Hegyi et al. |
| 8,714,975 | B2 | 5/2014 | Stumpel |
| D708,330 | S | 7/2014 | Jung |
| D713,034 | S | 9/2014 | Jung |
| 8,899,984 | B2 | 12/2014 | Llop et al. |
| 8,954,181 | B2 | 2/2015 | MacLeod et al. |
| 9,011,147 | B2 | 4/2015 | Jacquemyns |
| 9,011,148 | B2 | 4/2015 | Dolfi et al. |
| 9,044,296 | B2 | 6/2015 | Randall |
| 9,155,548 | B2 | 10/2015 | Lin |
| 9,468,504 | B2 | 10/2016 | Jung et al. |
| 9,549,785 | B2 | 1/2017 | Kim |
| 9,554,872 | B2 | 1/2017 | Koubi et al. |
| 9,848,965 | B2 | 12/2017 | Kim et al. |
| 9,901,417 | B2 | 2/2018 | Gantes |
| 2003/0216742 | A1 | 11/2003 | Wetzler et al. |
| 2004/0043355 | A1 | 3/2004 | Jonsson et al. |
| 2004/0219477 | A1 | 11/2004 | Harter |
| 2004/0219478 | A1 | 11/2004 | Harter |
| 2004/0219479 | A1 | 11/2004 | Malin et al. |
| 2005/0233276 | A1 | 10/2005 | Kopelman et al. |
| 2005/0282106 | A1 | 12/2005 | Sussman et al. |
| 2008/0287953 | A1 | 11/2008 | Sers |
| 2008/0287954 | A1 | 11/2008 | Kunz et al. |
| 2008/0312659 | A1 | 12/2008 | Metzger et al. |
| 2009/0181340 | A1 | 7/2009 | Wolf et al. |
| 2009/0274990 | A1 | 11/2009 | Kim |
| 2009/0291417 | A1 | 11/2009 | Rubbert et al. |
| 2010/0136500 | A1 | 6/2010 | Suter et al. |
| 2010/0173259 | A1 | 7/2010 | Vogel et al. |
| 2010/0185201 | A1 | 7/2010 | Kim |
| 2010/0192375 | A1 | 8/2010 | Jacquemyns |
| 2010/0196842 | A1 | 8/2010 | Jacquemyns |
| 2011/0112544 | A1 | 5/2011 | Haber |
| 2011/0212420 | A1 | 9/2011 | Vuillemot |
| 2012/0270176 | A1 | 10/2012 | Jacquemyns |
| 2013/0017507 | A1 | 1/2013 | Moffson et al. |
| 2014/0205968 | A1 | 7/2014 | Jung et al. |
| 2014/0215804 | A1 | 8/2014 | Jacquemyns |
| 2014/0248577 | A1 | 9/2014 | Tahmasebi et al. |
| 2014/0316750 | A1 | 10/2014 | Jung et al. |
| 2015/0257853 | A1 | 9/2015 | Jacquemyns |
| 2016/0157964 | A1 | 6/2016 | Suttin et al. |
| 2017/0000503 | A1 | 1/2017 | Keefer et al. |
| 2017/0165030 | A1 | 6/2017 | Liu |
| 2018/0177567 | A1 | 6/2018 | Klein et al. |
| 2018/0235726 | A1 | 8/2018 | Zastrow |
| 2018/0263526 | A1 | 9/2018 | Fares et al. |
| 2019/0125500 | A1 | 5/2019 | Oskam et al. |
| 2020/0113662 | A1 | 4/2020 | Clemens et al. |
| 2023/0248488 | A1 | 8/2023 | Ismael et al. |
| 2023/0263591 | A1 | 8/2023 | Fares et al. |
| 2023/0301758 | A1 | 9/2023 | Ismael et al. |

FOREIGN PATENT DOCUMENTS

| | | |
|---|---|---|
| DE | 4012327 A1 | 10/1991 |
| DE | 4013828 A1 | 1/1992 |
| DE | 102012003811 A1 | 8/2013 |
| EP | 1629793 A1 | 3/2006 |
| EP | 1796577 A1 | 6/2007 |
| EP | 2366358 A1 | 9/2011 |
| EP | 3235453 A1 | 10/2017 |
| JP | S63275335 A | 11/1988 |
| JP | H01059113 U | 4/1989 |
| JP | H08010268 A | 1/1996 |
| JP | 2006341067 A | 12/2006 |
| JP | 2009285358 A | 12/2009 |
| KR | 20180034872 A | 4/2018 |
| SI | 23494 A | 4/2012 |
| WO | 0234154 A2 | 5/2002 |
| WO | 2007104842 A1 | 9/2007 |
| WO | 2008038471 A1 | 4/2008 |
| WO | 2008149822 A1 | 12/2008 |
| WO | 2009000505 A1 | 12/2008 |
| WO | 2010086459 A1 | 8/2010 |
| WO | 2012110850 A2 | 8/2012 |
| WO | 2012162605 A2 | 11/2012 |
| WO | 2013181721 A2 | 12/2013 |
| WO | 2014113761 A1 | 7/2014 |
| WO | 2016094272 A1 | 6/2016 |
| WO | 2016142943 A1 | 9/2016 |
| WO | 2018012735 A1 | 1/2018 |
| WO | 2018170278 A2 | 9/2018 |
| WO | WO-2019020163 A1 * | 1/2019 |

OTHER PUBLICATIONS

Supplemental European Search Report issued in Appln. No. 20735991.0 dated Jul. 27, 2022 (2 pages).

* cited by examiner

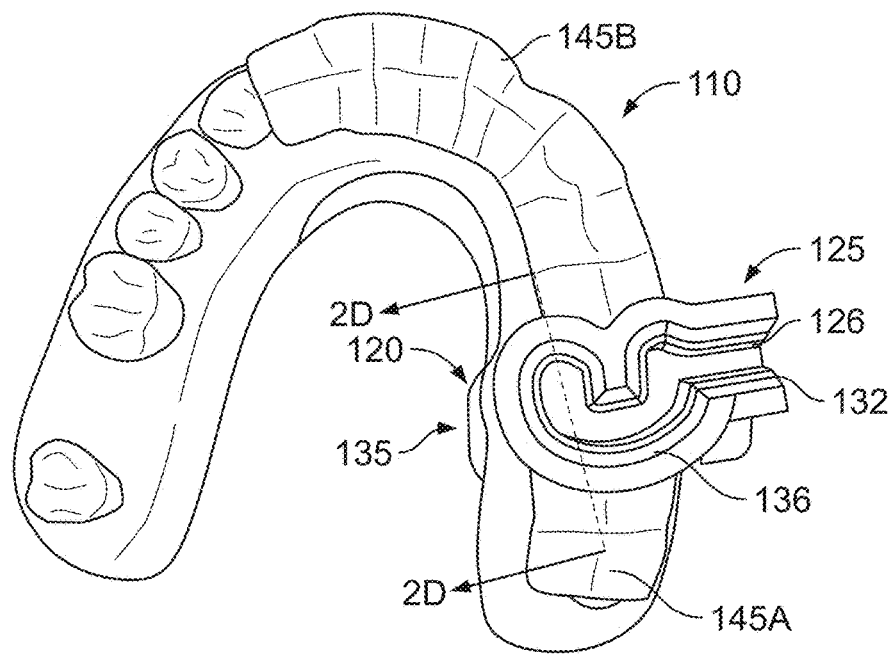
FIG. 2E
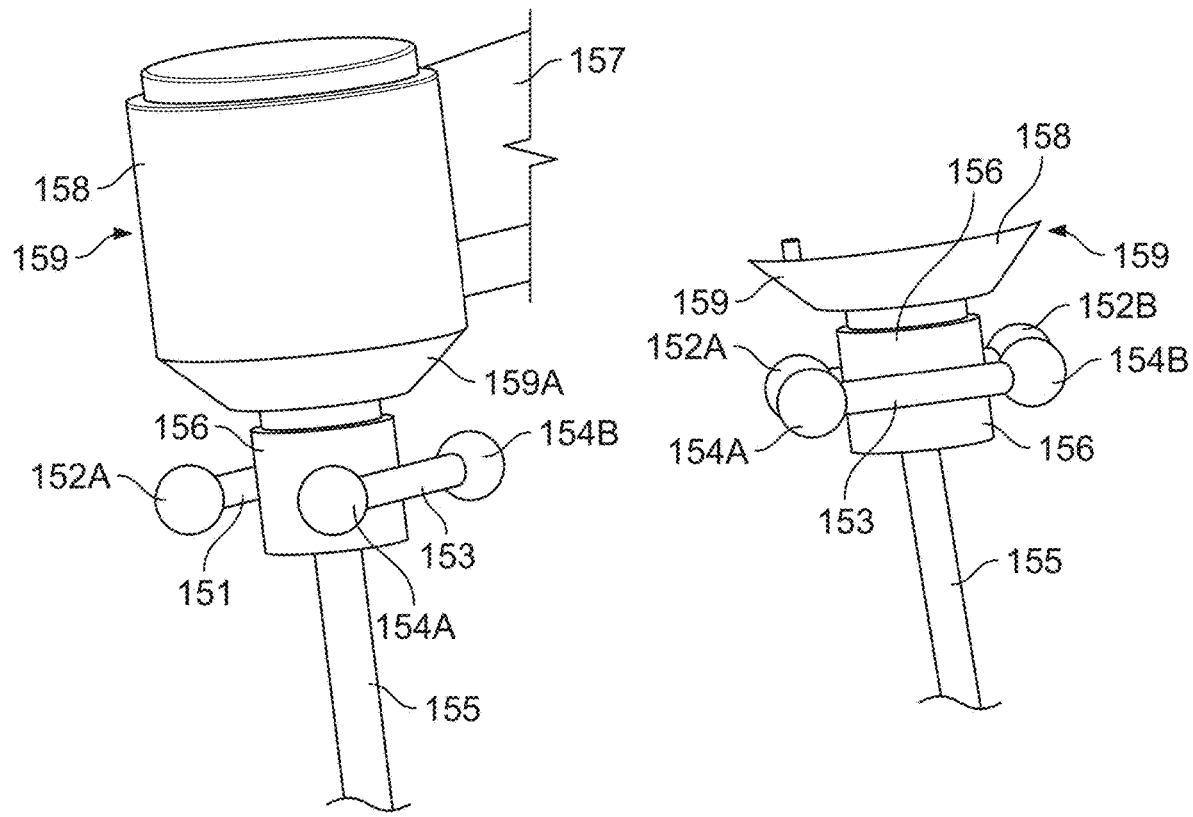
FIG. 3A
FIG. 3B

TOOTH PREPARATION SYSTEM WITH LATERAL PRONGS FOR LIMITING THREE-DIMENSIONAL MOVEMENT

CROSS-REFERENCE TO RELATED APPLICATIONS

The present application is a national phase entry under 35 U.S.C. § 371 of International Application No. PCT/US2020/012357, filed Jan. 6, 2020, published in English, which claims priority from U.S. Provisional Application No. 62/874,728, filed Jul. 16, 2019, and U.S. Provisional Application No. 62/788,318, filed Jan. 4, 2019, the entirety of the disclosures of all of which are hereby incorporated herein by reference.

FIELD OF THE TECHNOLOGY

The present technology relates to devices, systems, and processes for preparing a tooth for a tooth restoration, and in particular to instrumentation systems and processes for preparing such instrumentation systems for use in preparing a tooth to receive a tooth restoration.

BACKGROUND OF THE TECHNOLOGY

Complete, intact teeth that are cosmetically desirable, wear evenly, and provide a balanced bite are the objectives of dental patients. Over time, however, problems often arise in natural teeth due to accidents, deterioration from wear and tear, decay due to any one or any combination of poor oral hygiene, insufficient oral care practices, consumption of certain foods such as sweets, use of tobacco, disease, medications, certain congenital conditions, and environmental effects, tooth movement, etc. In some instances, natural teeth simply never achieve a cosmetic appearance desired by a patient. To this end, dental practitioners and their patients have relied on a variety of methods to repair these deformities and weaknesses of the patients' teeth.

The repair of teeth often requires preparation and modification of the exterior shape and size of a tooth to be able to receive various prostheses or restorations such as crowns, inlays, onlays, bridges, and veneers. Also, to prepare the appropriate prosthesis or restoration, either impressions or 3-dimensional scanning must be conducted of the original unmodified tooth and often the modified tooth at a later time. Dental practitioners often place a temporary prosthesis over the modified or prepared tooth while a permanent prosthesis is manufactured, but the use of such a temporary device and the removal of any cement used to place the temporary device over the prepared tooth may create a discrepancy between the prepared tooth and the internal configuration of the prosthesis.

Recently, systems and methods have been developed to form a guiding device for use in preparing a working tooth requiring treatment to receive a restoration along with the placement of a previously prepared restoration corresponding to the configuration of the guiding device during the same visit, thus obviating the need for a temporary prosthesis. Such systems, methods, and devices are disclosed in U.S. Patent Application Publication No. US2010/0192375 A1, now abandoned; U.S. Patent Application Publication No. US2010/0196842 A1, now U.S. Pat. No. 8,640,338; U.S. Patent Application Publication No. 2014/0248577 A1, and International Publication No. WO 2018/170278 A2, the disclosures of each of which are hereby incorporated by reference herein. Still, further improvements are needed to more efficiently and reliably treat the teeth of patients for receiving restorations and other prostheses.

SUMMARY OF THE TECHNOLOGY

In accordance with an aspect, a dental guide device may be configured for contacting a dental tool to limit the movement of the dental tool in the removal of a predetermined portion of tooth structure from a tooth to be treated in the mouth of a patient. The dental guide device may include an inner surface and a main body. The inner surface may be configured for attachment to a first tooth such that the dental guide device may be releasably fixable to the first tooth. The main body may be attached to the inner surface and may include a first guide channel, an aperture, and a first opening. The first guide channel may extend at least partially through the main body and may define a channel longitudinal axis. The first guide channel may be configured for contacting a first flange of the dental tool extending from a shaft of the dental tool to limit a movement of the dental tool. The first guide channel may define a first channel diameter in a first direction perpendicular to one or more directions the channel longitudinal axis may extend. The aperture may extend through the main body and may be configured to expose at least the predetermined portion of the tooth to be treated. The first opening may extend between the first guide channel and the aperture. The first opening may have a first opening diameter that may be less than the first channel diameter. The aperture may extend beyond the first opening in the first direction.

In some arrangements, the first opening may be configured for receiving a bar. In some such arrangements, the bar may extend from the shaft to the flange of the dental tool.

In some arrangements, the channel longitudinal axis may be curvilinear or linear.

In some arrangements, the first tooth may be the tooth to be treated such that the inner surface is configured for attachment to the tooth to be treated.

In some arrangements, the dental guide device may further include a tooth wrap. The tooth wrap may extend from the main body. In some such arrangements, the tooth wrap may include the inner surface and the first tooth may include one tooth or a plurality of teeth of the patient different from the tooth to be treated.

In some arrangements, a cross-section of the first guide channel may define an oval or a polygon. In some such arrangements, the cross-section of the first guide channel may define a circle.

In some arrangements, the first guide channel may extend through a sidewall of the main body to define an entryway configured for receipt of the dental tool into the first guide channel in a direction parallel to a direction the channel longitudinal axis extends through the entryway.

In some arrangements, the dental guide device may further include a passageway. The passageway may intersect the first guide channel and may extend through a sidewall of the body in a direction transverse to a direction the channel longitudinal axis extends at the intersection between the passageway and the first guide channel. The passageway may be configured for receipt of the flange of the dental tool through the passageway and into the first guide channel.

In some arrangements, the main body of the dental guide device may further include a second guide channel and a second opening. The second guide channel may extend at least partially through the main body. The second guide channel may be configured for contacting a second flange of the dental tool extending from the shaft of the dental tool to limit the movement of the dental tool. The second guide channel may define a second channel diameter in the first direction. The second opening may extend between the second guide channel and the aperture. The second opening may have a second opening diameter that may be less than the second channel diameter.

In some arrangements, the first and the second channel diameters may be the same. In some arrangements, a cross-section of the second guide channel may be a mirror image of a cross-section of the first guide channel.

In some arrangements, a cross-section of the second guide channel within a first plane may be spaced from a cross-section of the first guide channel within the first plane.

In some arrangements, the first and the second guide channels may intersect such that the second guide channel further defines the channel longitudinal axis.

In some arrangements, the first and the second guide channels may not intersect.

In some arrangements, the first and the second guide channels may extend through a sidewall of the body to define an entryway configured for receipt of the dental tool into the first and the second guide channels.

In some arrangements, the dental guide device may further include first and second passageways. The first and the second passageways may intersect the first and the second guide channels, respectively. The first and the second passageways may extend through a sidewall of the body in a direction transverse to the direction the channel longitudinal axis extends at the intersection between the first passageway and the first guide channel. The first and the second passageways may be configured for receipt of opposing first and second flanges of the dental tool through the first and the second passageways and into the first and the second guide channels, respectively.

In some arrangements, the first and the second flanges may be ends of a single bar.

In some arrangements, the dental guide device may further include third and fourth passageways. The third and the fourth passageways may extend through the sidewall of the body in the direction transverse to the direction the channel longitudinal axis extends at the intersection between the first passageway and the first guide channel. The third and the fourth passageways may intersect the first and the second guide channels at locations spaced apart from locations at which the first and the second passageways intersect the first and the second guide channels, respectively. The third and the fourth passageways may be configured for receipt of third and fourth flanges of the dental tool through the third and the fourth passageways and into the first and the second guide channels, respectively.

In some arrangements, the first and the second flanges may be ends of a single bar. In some arrangements including some arrangements in which the first and the second flanges are ends of the single bar, the third and the fourth flanges may be ends of a separate single bar.

In some arrangements, the first opening may be elongated.

In some arrangements, a longitudinal axis defined by the first opening within a cross-section of the device may extend at an oblique angle to a longitudinal axis defined by the aperture through the cross-section of the device.

In accordance with another aspect, a tooth preparation system configured for the removal of a predetermined portion of tooth structure from a tooth to be treated in the mouth of a patient to prepare the tooth to be treated for the placement of a restoration on the tooth to be treated may include a dental tool and a dental guide device. The dental tool may include a handpiece, opposing first and second flanges, and a cutting tool. The opposing first and second flanges may be attached to the handpiece. The cutting tool may be attached to the handpiece for removal of tooth structure. The cutting tool may define a central tool axis extending in a direction transverse to a direction each of the first and the second flanges extend. The dental guide device may be configured for contacting the dental tool to limit the movement of the dental tool in the removal of the predetermined portion of tooth structure from the tooth to be treated in the mouth of a patient. The dental guide device may include an inner surface and a main body. The inner surface may be configured for attachment to a first tooth such that the dental guide device is releasably fixable to the first tooth. The main body may be attached to the inner surface and may include a first guide channel, an aperture, a first opening, a second guide channel, and a second opening. The first guide channel may extend at least partially through the main body and may define a channel longitudinal axis. The first guide channel may be configured for contacting a first flange of the dental tool extending from a shaft of the dental tool to limit a movement of the dental tool and defining a first channel diameter in a first direction perpendicular to one or more directions the channel longitudinal axis extends. The aperture may extend through the main body and may be configured to expose at least the predetermined portion of the tooth to be treated. The first opening may extend between the first guide channel and the aperture. The first opening may have a first opening diameter in the first direction that is less than the first channel diameter. The aperture may extend beyond the first opening in the first direction. The second guide channel may extend at least partially through the main body. The second guide channel may be configured for contacting a second flange of the dental tool extending from the shaft of the dental tool to limit the movement of the dental tool. The second guide channel may define a second channel diameter in the first direction. The second opening may extend between the second guide channel and the aperture. The second opening may have a second opening diameter in the first direction that is less than the second channel diameter. The first and the second guide channels may include a curved section. The curved section may curve in a plane orthogonal to the central tool axis such that when the dental guide device is attached to the first tooth and the first and the second flanges of the dental tool are in contact with the first and the second guide channels, respectively, the first and the second guide channels limit the movement of the dental tool such that tooth structure is removable by the dental tool from any two sides of the tooth to be treated selected from the group consisting of the buccal, lingual, mesial, distal, and occlusal sides of the tooth to be treated.

In some arrangements, the central tool axis may extend orthogonally to a direction each of the first and the second flanges extend.

In some arrangements, the first and the second flanges may be integral with a portion of the handpiece such that each of the first and the second flanges may be inseparable from the handpiece without fracture of either one or both of the flange and the handpiece.

In some arrangements, the tooth preparation system may be part of a tooth restoration system that may further include a restoration for placement on the tooth to be treated after preparation of the tooth to be treated. In some such arrangements, the restoration may be a crown, in particular a "margin crown" that closely follows the gingival margin of a patient, a veneer, an inlay, an onlay, or a unit of a multi-unit bridge. In some arrangements, the first tooth may be the tooth or a plurality of teeth to be treated. Alternatively, the first tooth may be a different tooth than the tooth or the teeth to be treated.

In accordance with an aspect, a tooth preparation system configured for the removal of a predetermined portion of tooth structure from a tooth to be treated in the mouth of a patient to prepare the tooth to be treated for the placement of a restoration on the tooth to be treated may include a dental tool and a dental guide device. The dental tool may include a handpiece, opposing first and second flanges, and a cutting tool. The opposing first and second flanges may be attached to the handpiece. The cutting tool may be attached to the handpiece for removal of tooth structure. The cutting tool may define a central tool axis extending in a direction transverse to a direction each of the first and the second flanges extend. The dental guide device may be configured for contacting the dental tool to limit the movement of the dental tool in the removal of the predetermined portion of tooth structure from the tooth to be treated in the mouth of a patient. The dental guide device may include an inner surface and a main body. The inner surface may be configured for attachment to a first tooth such that the dental guide device is releasably fixable to the first tooth. The main body may be attached to the inner surface and may include a first guide channel, an aperture, a first opening, a second guide channel, and a second opening. The first guide channel may extend at least partially through the main body and may define a channel longitudinal axis. The first guide channel may be configured for contacting a first flange of the dental tool extending from a shaft of the dental tool to limit a movement of the dental tool and defining a first channel diameter in a first direction perpendicular to one or more directions the channel longitudinal axis extends. The aperture may extend through the main body and may be configured to expose at least the predetermined portion of the tooth to be treated. The first opening may extend between the first guide channel and the aperture. The first opening may have a first opening diameter in the first direction that is less than the first channel diameter. The aperture may extend beyond the first opening in the first direction. The second guide channel may extend at least partially through the main body. The second guide channel may be configured for contacting a second flange of the dental tool extending from the shaft of the dental tool to limit the movement of the dental tool. The second guide channel may define a second channel diameter in the first direction. The second opening may extend between the second guide channel and the aperture. The second opening may have a second opening diameter in the first direction that is less than the second channel diameter. Each of the first and the second guide channels may include a curved section. The curved section may curve in respective planes parallel to the central tool axis such that when the dental guide device is attached to the first tooth and the first and the second flanges of the dental tool are in contact with the first and the second guide channels, respectively, the first and the second guide channels limit the movement of the dental tool such that tooth structure is removable by the dental tool from the tooth to be treated at varying depths relative to a plane perpendicular to the central tool axis.

In some arrangements, the central tool axis may extend orthogonally to a direction each of the first and the second flanges extend.

In some arrangements, the first and the second flanges may be integral with a portion of the handpiece such that each of the first and the second flanges are inseparable from the handpiece without fracture of either one or both of the flange and the handpiece.

In some arrangements, the dental tool may be configured to travel within the dental guide device. In such arrangements, the first and the second guide channels may limit the movement of the dental tool during the travel of the dental tool within the guide device such that tooth structure is removable by the dental tool from the tooth to be treated a fixed distance above a gingival margin of a patient over a discrete distance that the dental tool is configured to travel within the dental guide device.

In some arrangements, the tooth preparation system may be part of a tooth restoration system that may further include a restoration for placement on the tooth to be treated after preparation of the tooth to be treated. In some such arrangements, the restoration may be a crown, in particular a "margin crown" that closely follows the gingival margin of a patient, a veneer, an inlay, an onlay, or a unit of a multi-unit bridge. In some arrangements, the first tooth may be the tooth or a plurality of teeth to be treated. Alternatively, the first tooth may be a different tooth than the tooth or the teeth to be treated.

In accordance with another aspect, a dental guide device may be configured for contacting a dental tool to limit the movement of the dental tool in the removal of a predetermined portion of tooth structure from a tooth to be treated in the mouth of a patient. The dental guide device may include an inner surface and a main body. The inner surface may be configured for attachment to a first tooth such that the dental guide device may be releasably fixable to the first tooth. The main body may be attached to the inner surface and may include a passageway, a first slot, a second slot, and an aperture. The passageway may extend at least partially through the main body. The first slot may extend through a surface of the main body and into the passageway. The second slot may extend through a surface of the main body and into the passageway. The first and the second slots may define respective longitudinal axes intersecting or parallel to each other within a cross-section of the guide device through the first and the second slots and further may be configured to receive bars of a dental tool. The aperture may extend through the main body and may be configured to expose at least the predetermined portion of the tooth to be treated. The passageway may be configured to contact the bars of the dental tool to limit the movement of the dental tool to remove at most the predetermined portion of tooth structure to be removed from the tooth to be treated.

In some arrangements, the first tooth may be the tooth to be treated or a plurality of teeth to be treated. In this manner, the first tooth may be configured for attachment to the tooth to be treated or the plurality of teeth to be treated as the case may be.

In some arrangements, a tooth wrap may extend from the main body. In such arrangements, the tooth wrap may include the inner surface and the first tooth may include a tooth of the patient different from the tooth or the teeth to be treated.

In accordance with another aspect, a tooth preparation system for the removal of a predetermined portion of tooth structure from a tooth to be treated in the mouth of a patient to prepare the tooth to be treated for the placement of a restoration on the tooth to be treated may include a dental tool and a dental guide device. The dental tool may include a handpiece, a first bar, and a second bar. The handpiece may include a main shaft that may define a central axis. The first bar may be attached to the main shaft and may extend in a first direction transverse to a direction the central axis extends. The first bar may define a first bar end configured for receipt into and contact with a dental guide device. The second bar may be attached to the main shaft and may extend in a second direction transverse to the direction the central axis extends. The second bar may define a second bar end configured for receipt into and contact with a dental guide device. The first bar may define a first longitudinal axis and the second bar may define a second longitudinal axis. The first and the second longitudinal axes may be in different planes parallel to a plane including the central axis or in different planes each including the central axis. The dental guide device may be configured for contacting the dental tool to limit the movement of the dental tool in the removal of a predetermined portion of tooth structure from a tooth to be treated in the mouth of a patient. The dental guide device may include an inner surface and a main body. The inner surface may be configured for attachment to a first tooth such that the dental guide device may be releasably fixable to the first tooth. The main body may be attached to the inner surface and may include a passageway, a first slot, a second slot, and an aperture. The passageway may extend at least partially through the main body. The first slot may extend through a surface of the main body and into the passageway. The second slot may extend through a surface of the main body and into the passageway. The first and the second slots may define respective longitudinal axes intersecting or parallel to each other and may be configured to receive bars of a dental tool. The aperture may extend through the main body and may be configured to expose at least the predetermined portion of the tooth to be treated. The passageway may be configured to contact the bars of the dental tool to limit the movement of the dental tool to remove at most the predetermined portion of tooth structure to be removed from the tooth to be treated. The first slot and the second slot of the dental guide device may be configured to simultaneously receive the first bar and the second bar of the dental tool.

In accordance with another aspect, a dental cutting tool configured for contacting a dental guide device to guide the dental cutting tool may include a main shaft, a first bar, and a second bar. The main shaft may define a central axis. The first bar may be attached to the main shaft and may extend in a first direction transverse to a direction the central axis extends. The first bar may define a first bar end configured for receipt into and contact with the dental guide device. The second bar may be attached to the main shaft and may extend in a second direction transverse to the direction the central axis extends. The second bar may define a second bar end configured for receipt into and contact with the dental guide device. The first bar may define a first longitudinal axis, and the second bar may define a second longitudinal axis. The first and the second longitudinal axes may be in different planes parallel to a plane including the central axis or in different planes each including the central axis.

In some arrangements, the first and the second directions may be the same direction. In some arrangements, the first direction and the second direction may be perpendicular to the central axis.

In some arrangements, the dental cutting tool may further include a third bar. The third bar may be attached to the main shaft and may extend in a third direction transverse to the direction the central axis extends. Each of the first, the second, and the third directions may be different.

In some arrangements, the first, the second, and the third bars may be equally spaced circumferentially from each other within a projection of the first, the second, and the third bars onto a plane.

In some arrangements, the first bar and the second bar may define respective longitudinal axes that form an angle of at least 90 degrees with respect to each other within a projection of the first and the second bars onto a plane.

In some arrangements, the dental cutting tool may further include opposing partial spheres on ends of each of the first and the second bars.

In some arrangements, the dental cutting tool may further include a first partial cylinder, partial ovular prism, or partial polyhedron on an end of each of the first and the second bars opposing a second partial cylinder, partial ovular prism, or partial polyhedron on an opposing end of each of the first and the second bars.

In some arrangements, the dental cutting tool may further include a dental bur extending at least partially through the main shaft.

In some arrangements, the first bar and the second bar may be integral with the main shaft such that the first bar, the second bar, and the main shaft may be inseparable without fracture of any one or any combination of the first bar, the second bar, and the main shaft.

In accordance with another aspect, a tooth preparation system for the removal of a predetermined portion of tooth structure from a tooth to be treated in the mouth of a patient may include a dental cutting tool and a dental guide device. The dental cutting tool may be configured for contacting a dental guide device to guide the dental cutting tool. The dental cutting tool may include a main shaft, a first bar, and a second bar. The main shaft may define a central axis. The first bar may be attached to the main shaft and may extend in a first direction transverse to a direction the central axis extends. The first bar may define a first bar end configured for receipt into and contact with the dental guide device. The second bar may be attached to the main shaft and may extend in a second direction transverse to the direction the central axis extends. The second bar may define a second bar end configured for receipt into and contact with the dental guide device. The first bar may define a first longitudinal axis, and the second bar may define a second longitudinal axis. The first and the second longitudinal axes may be in different planes parallel to a plane including or in different planes each including the central axis. The dental guide device may include an inner surface and a main body. The inner surface may be configured for attachment to a first tooth such that the dental guide device may be releasably fixable to the first tooth. The main body may be attached to the inner surface and may include a first guide channel, an aperture, a first opening, a second guide channel, and a second opening. The first guide channel may extend at least partially through the main body and may define a channel longitudinal axis. The first guide channel may be configured for contacting the first bar of the dental cutting tool to limit a movement of the dental cutting tool. The first guide channel may define a first channel diameter in a first direction perpendicular to directions the channel longitudinal axis extends. The aperture may extend through the main body and may be configured to expose at least the predetermined portion of the tooth to be treated. The first opening may extend between the first guide channel and the aperture. The first opening may have a first opening diameter that is less than the first channel diameter. The second guide channel may extend at least partially through the main body. The second guide channel may be configured for contacting the second bar of the dental cutting tool to limit the movement of the dental cutting tool. The second guide channel may define a second channel diameter in the first direction. The second opening may extend between the second guide channel and the aperture. The second opening may have a second opening diameter that is less than the second channel diameter.

A dental guide device for contacting a dental tool to limit the movement of the dental tool in the removal of a predetermined portion of tooth structure from a tooth to be treated in the mouth of a patient may include an inner surface and a main body. The inner surface may be configured for attachment to a first tooth such that the dental guide device is releasably fixable to the first tooth. The main body may be attached to the inner surface and may include a first guide channel, an aperture, a second guide channel, and a third guide channel. The first guide channel may extend at least partially through the main body and may define a channel longitudinal axis. The first guide channel may be configured for contacting a first bar of the dental tool to limit a movement of the dental tool and may define a first channel diameter in a first direction perpendicular to directions the channel longitudinal axis extends. The aperture may extend through the main body and may be configured to expose at least the predetermined portion of the tooth to be treated. The second guide channel may extend at least partially through the main body on a side of the aperture opposite the first guide channel. The second guide channel may be configured for contacting a second bar of the dental tool to limit the movement of the dental tool and may define a second channel diameter in the first direction. The third guide channel may extend at least partially through the main body on the same side of the aperture as the first guide channel. The third guide channel may be below the first guide channel. The third guide channel may be configured for contacting a third bar of the dental tool to limit the movement of the dental tool and may define a third channel diameter in the first direction.

In some arrangements, the main body of the dental guide device may include a fourth guide channel that may extend at least partially through the main body on the same side of the aperture as the second guide channel. The fourth guide channel may be below the second guide channel. The fourth guide channel may be configured for contacting a fourth bar of the dental tool to limit the movement of the dental tool and may define a fourth channel diameter in the first direction.

In some arrangements, at least the first channel diameter, the second channel diameter, and the third channel diameter may be the same diameter.

In some arrangements, the dental guide device may further include a first opening, a second opening, and a third opening. The first opening may extend between the first guide channel and the aperture. The first opening may have a first opening diameter that may be less than the first channel diameter. The second opening may extend between the second guide channel and the aperture. The second opening may have a second opening diameter that may be less than the second channel diameter. The third opening may extend between the third guide channel and the aperture. The third opening may have a third opening diameter that may be less than the third channel diameter. Longitudinal axes defined by each of the first opening, the second opening, and the third opening within a cross-section of the dental guide device may extend at oblique angles to a longitudinal axis defined by the aperture through the cross-section of the dental guide device.

In some arrangements, longitudinal axes defined by each of the first guide channel, the second guide channel, and the third guide channel within a cross-section of the dental guide device may extend at oblique angles to a longitudinal axis defined by the aperture through the cross-section of the dental guide device.

In accordance with another aspect, a dental guide device configured for contacting a dental tool to limit the movement of the dental tool in the removal of a predetermined portion of tooth structure from a tooth to be treated in the mouth of a patient may include a body that may include an inner surface and a channel. At least a portion of the inner surface may be configured for releasable attachment to a first tooth. The channel may extend through the inner surface. The channel may define a central region and first and second annex regions spaced from the central region for introduction of a dental tool. Each of the first and the second annex regions may be in communication with the central region via respective first and second openings. The central region may have a first height taken in a first direction. The first annex region may have a second height taken in a first direction that is less than the first height. The first opening may have a third height taken in the first direction that is less than the second first height. The second annex region may have a fourth height taken in the first direction that is less than the first height. The second opening may have a fifth height taken in the first direction that is less than the further height.

In some arrangements, the first tooth may be the tooth to be treated or a plurality of teeth to be treated. Alternatively, the first tooth may be a different tooth than the tooth to be treated or the plurality of the teeth to be treated as the case may be.

In some arrangements, the dental tool may include a cutting tool that defines a longitudinal axis. In such arrangements, the first and the second annex regions may be offset from the longitudinal axis. In some such arrangements, a tooth preparation system for the removal of a predetermined portion of tooth structure from a tooth to be treated in the mouth of a patient may include the dental cutting tool and the dental guide device.

BRIEF DESCRIPTION OF THE DRAWINGS

A more complete appreciation of the subject matter of the present technology and the various advantages thereof may be realized by reference to the following detailed description which refers to the accompanying drawings, in which:

FIG. 2E is a plan view of the tooth preparation guide of FIGS. 2A-2D;

FIGS. 3A and 3B are perspective views of a dental tool of the tooth preparation system of FIGS. 1A and 1B in accordance with another embodiment;

DETAILED DESCRIPTION

Figure 1A:
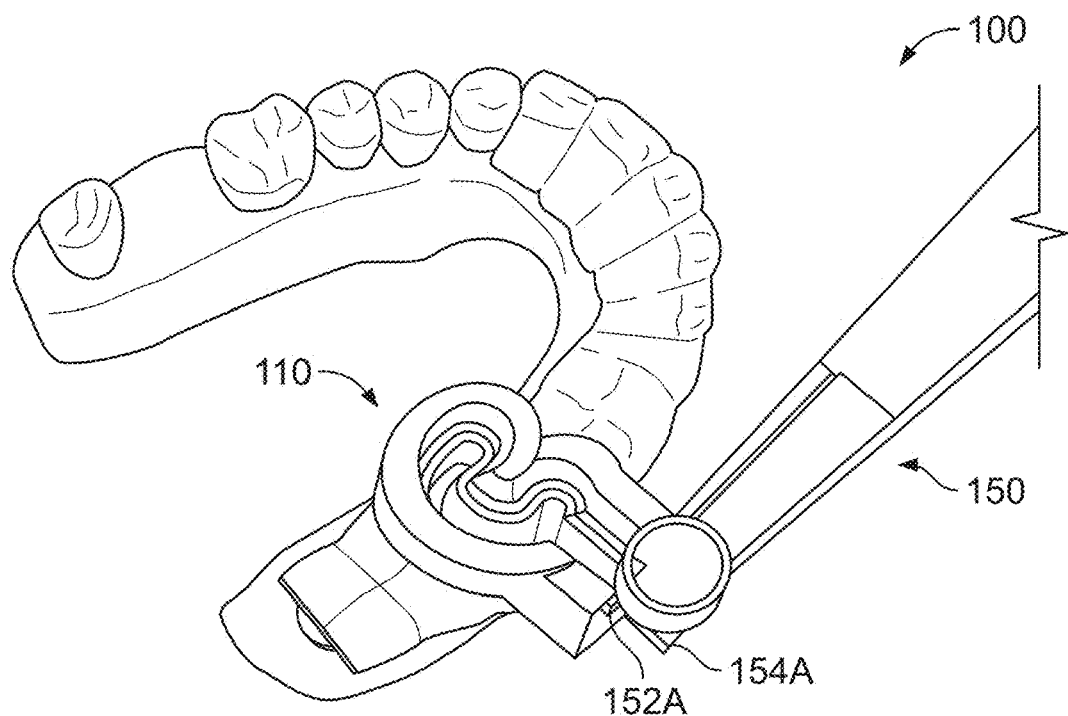
FIGS. 1A-1C are perspective views of a tooth preparation system in accordance with an embodiment.
Figure 1B:
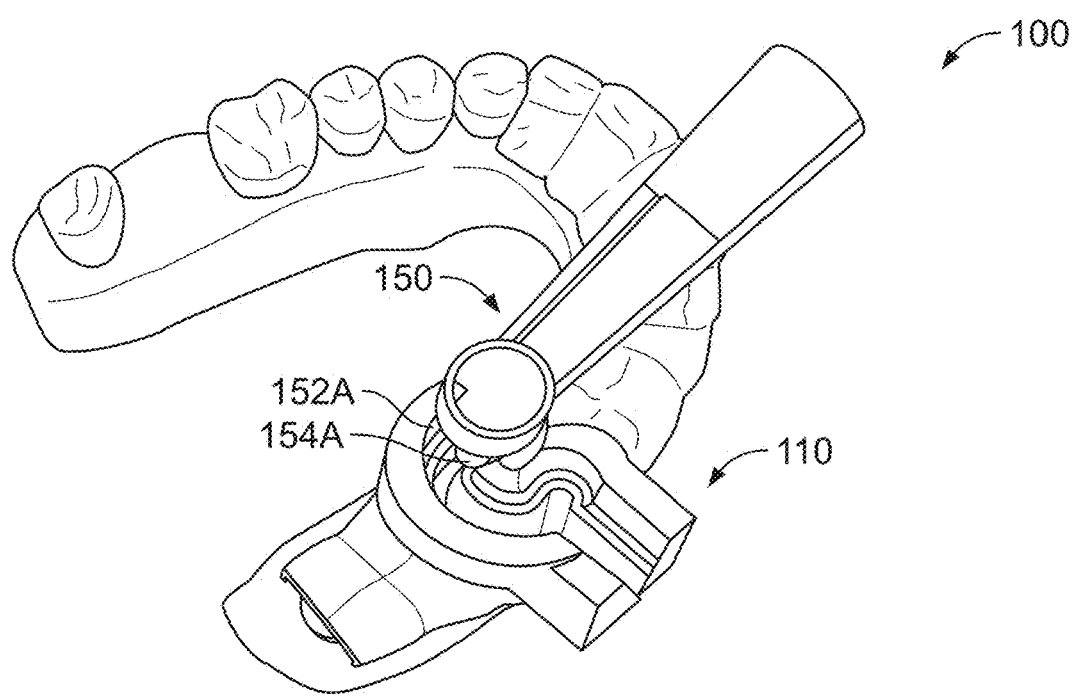
Figure 1C:
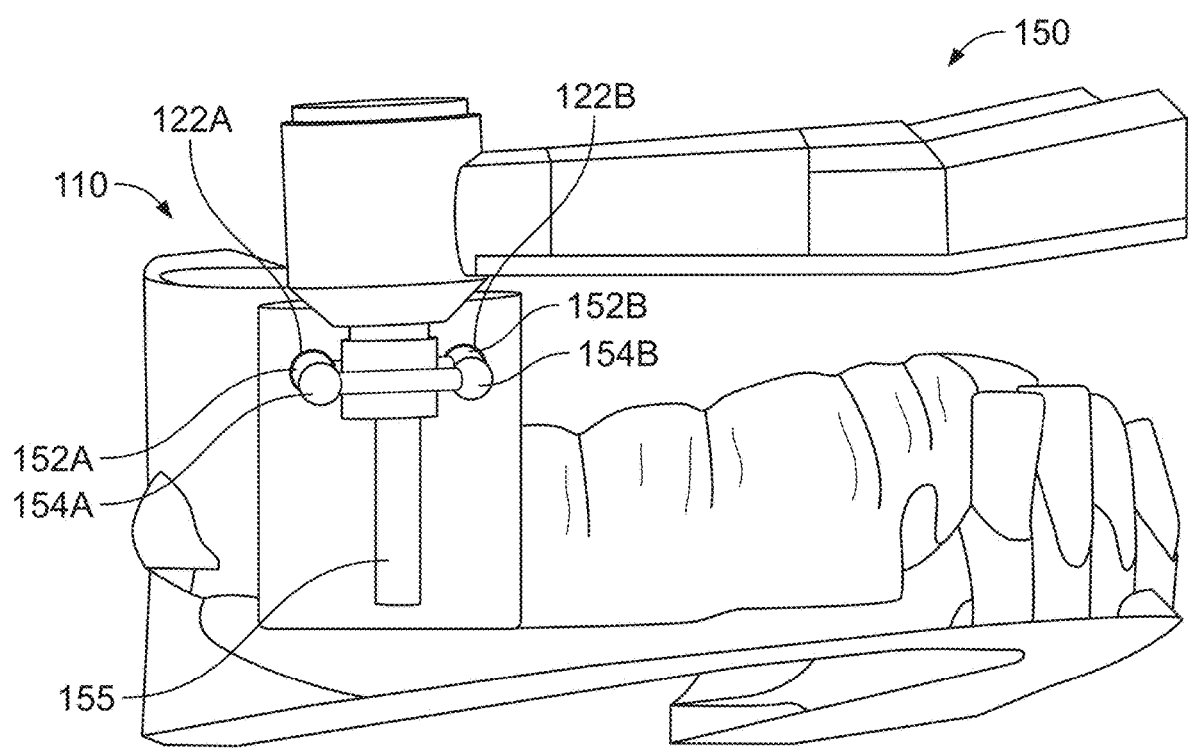

Referring now to FIGS. 1A-1C, tooth preparation system 100 includes tooth preparation guide 110 and dental tool 150 configured to be guided by the tooth preparation guide in removing tooth structure from one or more working teeth to be treated in the mouth of a patient. In the example shown, guide 110 is configured for contacting a dental tool, such as dental tool 150, to guide the dental tool along a predetermined path in the removal of the distal side and portions of the buccal and lingual sides of a tooth to be treated (or in some arrangements, a plurality of teeth to be treated), and thereby in the removal of a portion of an occlusal surface of the tooth to be treated, in preparing the tooth to be treated to receive a crown, in particular a "margin crown" as described previously herein, a veneer, an inlay, an onlay, or a unit of a multi-unit bridge. In some alternative arrangements, a guide in accordance with the present technology may be fabricated for use in contacting a dental tool to guide the dental tool along a predetermined path in removing tooth structure from one or more teeth to be treated to prepare the one or more teeth to be treated to receive any one of various restorations including but not limited to (i) a crown in which tooth structure may be removed from the tooth to be treated with an alternative approach to that shown in FIGS. 1A and 1B, (ii) a veneer in which at least a portion of a buccal surface of the tooth to be treated may be removed, or (iii) a bridge in which tooth structure from adjacent teeth to be treated may be removed to receive the bridge between the adjacent teeth.

As shown in FIGS. 2A-2D, tooth preparation guide 110 is configured for removing tooth structure from a first molar of a patient, and thus includes main body 120, distal wrap 145A extending from a distal side of the main body, and mesial wrap 145B extending from a mesial side of the base, which may be prepared in the manner disclosed in U.S. Patent Application Publication No. 2018/0263726 A1 ("the '726 Application"), the entire disclosure of which is hereby incorporated by reference herein. As shown, distal wrap 145A includes distal inner surface 146A extending from a lingual side to a buccal side of a second molar of the patient and substantially matching a contour of the surfaces of the second molar over which the distal inner surface extends. Similarly, mesial wrap 145B includes a mesial inner surface (not shown) that extends from a lingual side to a buccal side of each of the set of the teeth adjacent to the first molar of the patient in the mesial direction that include the lateral incisor on the opposite side of the mouth of the patient, i.e., from the second premolar (bicuspid) to the lateral incisor such that portions of both lateral incisors are covered. As in the example shown, the mesial inner surface of mesial wrap 145B may substantially match a contour of the surfaces over which the mesial inner surface extends.

In some alternative arrangements, the tooth preparation guide may include a main body that covers a tooth or even a set of teeth to be treated different than a single first molar and, accordingly, may include one or more wraps that cover and substantially match a contour of different teeth than those covered by distal wrap 145A and mesial wrap 145B such that the wrap is releasably fixed to the teeth, i.e., extends around the crown of one or more of the teeth so as to be adequately in contact with the teeth and so that, once applied, the wrap will not be released even if certain pressure, due to a normal use of the overlay, is applied. In some such arrangements, the tooth preparation guide may include only one wrap, such as in the example when the tooth to be treated is a second molar in which example only a mesial wrap may be attached to the base covering the tooth to be treated.

As further shown, main body 120 includes insertion section 125 configured to receive a dental tool, such as but not limited to dental tool 150, and operable section 135. In the example shown, insertion section 125 of main body 120 includes opposing guide channels 122A, 122B, head channel 124, tool channel 126, opposing flange openings 127A, 127B, and opposing chamfered edges 128A, 128B. As shown, each of opposing guide channels 122A, 122B, head channel 124, tool channel 126, opposing flange openings 127A, 127B, and opposing chamfered edges 128A, 128B extend through sidewall 130 of insertion section 125 to define entryway 132 and extend through the insertion section to operable section 135 such that they pass through a thickness of the insertion section. In the example shown, operable section 135 of main body 120 includes opposing guide channels 122A, 122B as such channels continue from insertion section 125, head channel 124 as such channel continues from the insertion section, tool aperture 136, opposing flange openings 127A, 127B as such openings continue from the insertion section, and opposing chamfered edges 128A, 128B as such edges continue from the insertion section.

As shown, opposing guide channels 122A, 122B extend partially through operable section 135, define channel longitudinal axes, and are configured to receive and to contact opposing flanges of a dental tool. In this example, the portions of the longitudinal axes defined by opposing guide channels 122A, 122B in insertion section 125 are linear and parallel whereas the portions of the longitudinal axes defined by the opposing guide channels in operable section 135 are curvilinear and non-parallel but generally in a similar direction until the opposing guide channels converge or at least end at respective end portions 123 in the operable section. In this manner, with reference to FIG. 1A, insertion section 125 of main body 120 of guide 110 may receive dental tool 150 and, with reference to FIG. 1B, end portion 123 of operable section 135 of the main body may limit the total travel of the dental tool within guide 110. In some alternative arrangements, the opposing guide channels may intersect within end portion 123 such that the opposing guide channels define a common longitudinal axis or may extend through a thickness of the main body of the tooth preparation guide such that a dental tool may be removed from the main body at a different location than the entryway of the main body, in contrast to arrangements such as guide 110 in which a dental tool is both inserted and removed from entryway 132. In any such arrangements, each channel longitudinal axis may be linear or curvilinear along any portion of the channel longitudinal axis.

As in the example shown, a cross-section of each of opposing guide channels 122A, 122B is substantially circular in order to receive a complementary spherical flange of a dental tool, such as one of opposing first flanges 152A, 152B and consecutively one of opposing second flanges 154A, 154B of dental tool 150 described further herein. Opposing guide channels 122A, 122B each define a guide channel diameter in a first direction transverse, and as shown perpendicular, to the channel longitudinal axis. In certain alternative arrangements, a cross-section of one or both of the opposing guide channels may define a different shape such as but not limited to an oval different from a circle or a polygon, whether regular or irregular that may correspond to differently shaped flanges of a dental tool.

Figure 2A:
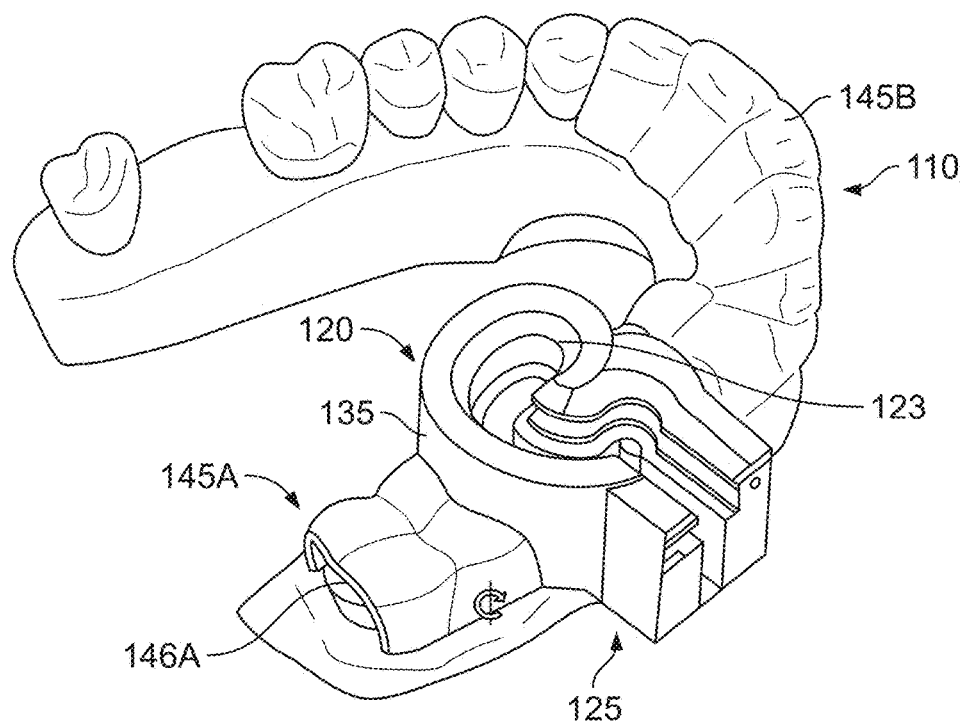
FIG. 2A-2C are perspective views of a tooth preparation guide of the tooth preparation system of FIGS. 1A and 1B in accordance with another embodiment.
Figures 2B, 2C:
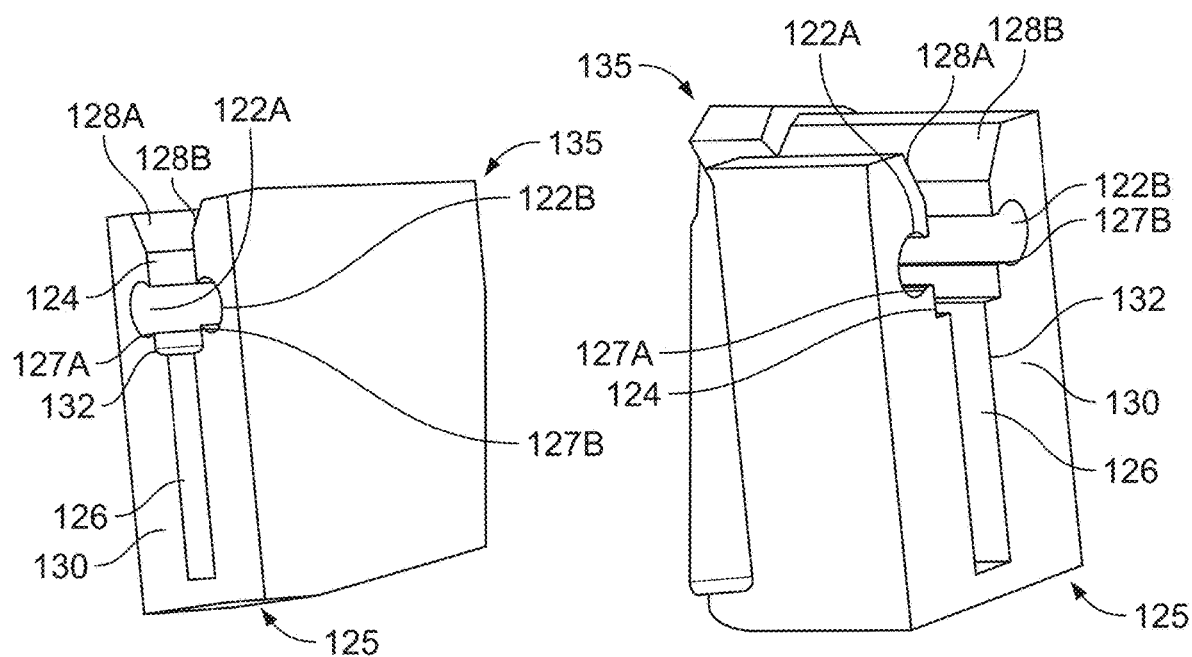
Figure 2D:
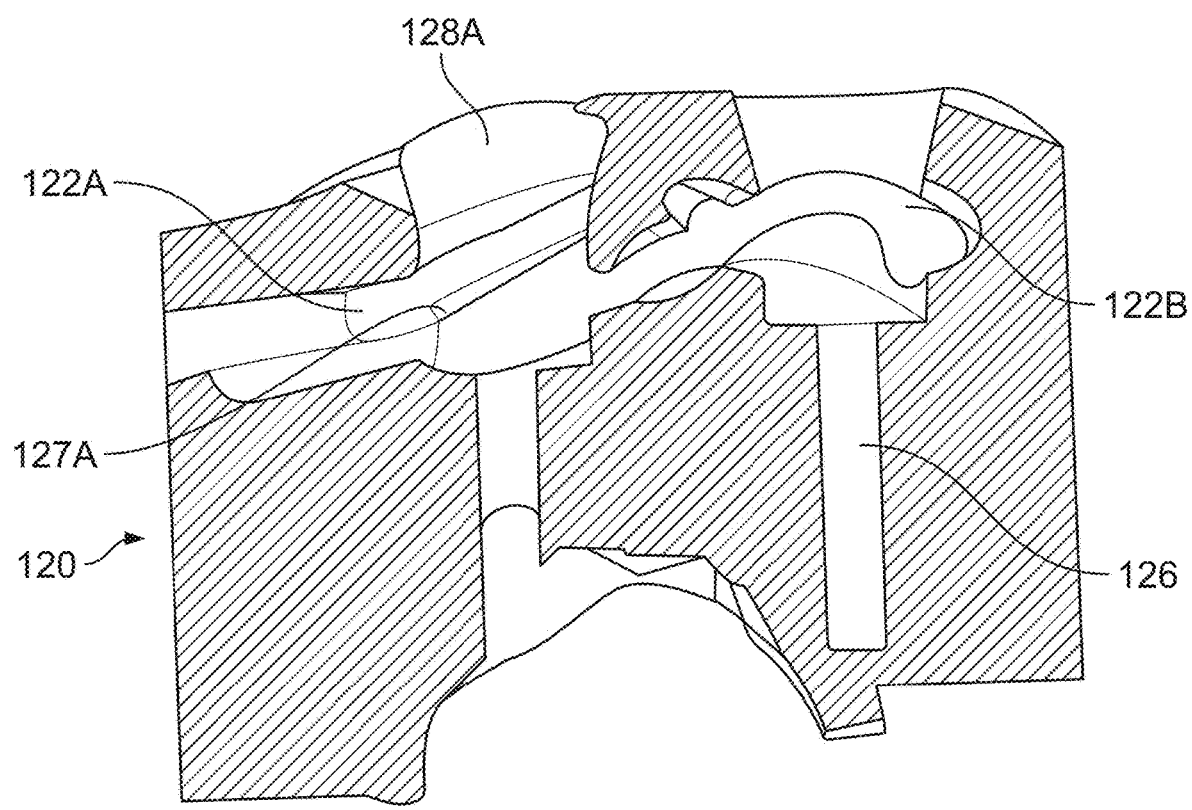
FIG. 2D is a cross-sectional elevation view of the tooth preparation guide of FIGS. 2A-2C taken along lines 2D-2D as shown in FIG. 2E.

In the example shown, head channel 124 extends between and is defined by central walls of main body 120 generally above and below opposing guide channels 122A, 122B, respectively. As in this example, head channel 124 may be configured for receiving guide head 156 of dental tool 150 described further herein or a similarly shaped portion of a dental tool along a length of the head channel. Tool channel 126 extends from head channel 124 and, as in this example, may be substantially greater in depth than in width (within a plane perpendicular to longitudinal axes of opposing guide channels 122A, 122B) for receiving cutting tool 155 of dental tool 150 described further herein or other tools having a similar profile. As in the example shown, tool channel 126 may extend to and transition to tool aperture 136 providing an opening for exposing the tooth to be treated or plurality of teeth to be treated for the removal of tooth structure from the tooth or teeth to be treated. As best shown in FIG. 2D, in some arrangements such as in the example shown, tool channel 126 may extend only within insertion section 125, and tool aperture 136 may extend only within operable section 135. Tool channel 126 may have a sufficient width in a direction between the opposing walls defining the tool channel, as in the example shown, such that the tool channel receives cutting tool 155 along a length of the tool channel in a direction parallel to the longitudinal axes of opposing guide channels 122A, 122B without the dental tool contacting the tool channel. As best shown in FIGS. 2B and 2C, opposing chamfered edges 128A, 128B extend from the respective walls defining head channel 124 to define an upper opening and clearance for a shaft or housing of a dental tool such as but not limited to housing 158 of main head 159 of dental tool 150.

As also best shown in FIGS. 2B and 2C, each of opposing flange openings 127A, 127B extends between head channel 124 and a respective one of the opposing guide channels 122A, 122B. Each of flange openings 127A, 127B may have an opening diameter in the first direction, which may be a height of each flange opening, that is less than a guide channel diameter of its adjacent guide channel 122A, 122B, which may be a height of each of the guide channels. In some arrangements, the opening diameter may be a maximum height of the flange openings, and in some arrangements, the guide channel diameter may be a maximum height of the guide channels.

In insertion section 125, opposing chamfered edges 128A, 128B, head channel 124, and tool channel 126 define a central channel or insertion central region having a volume within the insertion section. Similarly, in operable section 135, opposing chamfered edges 128A, 128B, head channel 124, and tool aperture 136 define a central aperture or operable central region having a volume within the operable section. Each of the insertion and operable central regions define an overall central region collectively. Each of guide channels 122A, 122B define first and second insertion and first and second operable annex regions on opposing sides of the insertion section 125 and the operable section 135, respectively, in which the first insertion annex region and the first operable annex region define a first overall annex region and the second insertion annex region and the second operable annex region define a second overall annex region. In this context and in the example of FIGS. 1A-2D, heights of the flange openings between the insertion central region and the first insertion annex region and between the insertion central region and the second insertion annex region are less than respective heights of the first and the second insertion annex regions to which they are adjacent. Similarly, heights of the flange openings between the operable central region and the first operable annex region and between the operable central region and the second operable annex region are less than the respective heights of the first and the second operable annex regions to which they are adjacent.

Referring now to FIGS. 3A and 3B, dental tool 150 may be in the form of a dental handpiece that includes handle 157, main head 159, guide head 156, first connection bar 151, opposing first flanges 152A, 152B, second connection bar 153, opposing second flanges 154A, 154B, and cutting tool 155. In the example shown, main head 159 extends from handle 157 and may be a drive head having a main shaft attached to cutting tool 155 for providing high-speed rotation to the cutting tool in a manner similar to other dental handpieces known to those skilled in the art. As further shown, main head 159 includes housing 158 having head chamfer 159A facing towards cutting tool 155. Head chamfer 159A may correspond to chamfered edges 128A, 128B when dental tool 150 is fully and properly inserted into tooth preparation guide 110. Guide head 156 extends from main head 159 to provide a base for first and second connection bars 151, 153 attached to the guide head. As in the example shown, in some arrangements, a combination of first connection bar 151 and opposing first flanges 152A, 152B may be identical or at least substantially identical to a combination of second connection bar 153 and opposing second flanges 154A, 154B. As shown, each of opposing first flanges 152A, 152B and opposing second flanges 154A, 1524B may be in the form of partial spheres such that they have circular cross-sections to correspond with opposing guide channels 122A, 122B such that the flanges fit closely within the corresponding guide channels. In some alternative arrangements, any one or any combination of such flanges may be but are not limited to being in the form of partial cylinders, partial ovular prisms, partial polyhedrons, or irregular shapes in which the opposing guide channels of a corresponding tooth preparation guide have cross-sections that correspond with cross-sections of such flanges such that the flanges fit closely within the corresponding guide channels.

As best shown in FIG. 3B, first and second connection bars 151, 153 are attached to guide head 156 at their respective centers, although in some alternative arrangements, the first and the second connection bars may be attached to the guide head at positions offset from the center depending on the needs of the patient. As in the example shown, first and second connection bars 151, 153 may be welded to guide head 156, although in alternative arrangements, the connection bars may be attached by a fastener such as but not limited to a screw or by other attachment means known to those skilled in the art. As shown, first and second connection bars 151, 153 extend in a direction orthogonal to a direction in which a longitudinal axis defined by cutting tool 155 extends, although in some alternative arrangements, the connection bars may extend in other directions transverse to a direction in which the longitudinal axis defined by the cutting tool extends. As further shown, cutting tool 155, which may be a dental bur, extends below guide head 156 such that the cutting tool is uncovered below a substantial portion of its length.

Referring again to FIG. 1A, in using tooth preparation system 100, dental tool 150 preferably may be inserted into tooth preparation guide 110 such that first connection bar 151 and opposing first flanges 152A, 152B are inserted into entryway 132 together and second connection bar 153 and opposing second flanges 154A, 154B are inserted into the entryway together either before or after the combination of the first connection bar and the opposing first flanges are inserted into the entryway. As demonstrated by FIG. 1C, when dental tool 150 is inserted into guide 110, each of the first and the second connection bars 151, 153 are received and maintained in both opposing flange openings 127A, 127B while each of opposing first flanges 152A, 152B are received and maintained in opposing guide channels 122A, 122B, respectively, and each of opposing second flanges 154A, 154B are also received and maintained in opposing guide channels 122A, 122B, respectively, while the dental tool travels through the guide. In this manner, opposing first flanges 152A, 152B and opposing second flanges 154A, 154B contact opposing guide channels 122A, 122B such that the guide channels guide the first and the second flanges and thereby guide dental tool 150 along a predetermined path set by the opposing guide channels. Such a predetermined path may be in directions perpendicular to the longitudinal axis of cutting tool 155 of dental tool 150, in directions parallel to the longitudinal axis of the cutting tool, and in direction transverse to the longitudinal axis of the cutting tool. As dental tool 150 travels along the predetermined path, cutting tool 155 may remove predetermined tooth structure from the tooth to be treated.

In some arrangements, either one or a combination of first connection bar 151 and second connection bar 153 may be dimensioned, and further, opposing flange openings 127A, 127B may be dimensioned, such that the opposing flange openings contact either one or both of the first connection bar and the second connection bar to limit the movement of the contacted one or both of the first connection bar and the second connection bar in a direction parallel to the longitudinal axis of cutting tool 155 during travel of dental tool 150 through guide 110. In other arrangements, the first connection bar 151, second connection bar 153, and opposing flange openings 127A, 127B may be dimensioned to provide clearance such that the connection bars do not contact the opposing flange openings during travel of dental tool 150 through guide 110.

Figure 11:
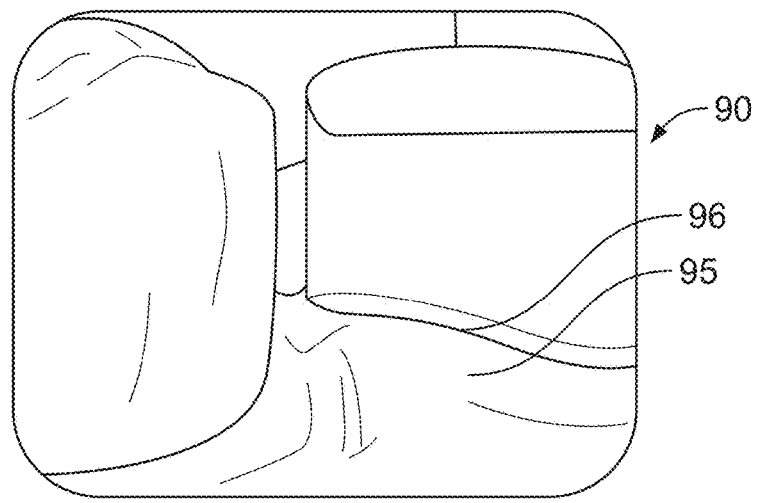
FIG. 11 is a perspective view of a prepared tooth following use of the tooth preparation system of FIGS. 1A and 1B on a tooth to be treated.

With reference to FIG. 11, using guide 110, tooth structure may be removed from buccal, distal, and lingual sides of a tooth to be treated, and thereby to remove a portion of the occlusal surface of the tooth to be treated to form tooth 90, as shown. In the example as shown, in so removing the tooth structure, opposing guide channels 122A, 122B of guide 110 contacted dental tool 150 to guide the dental tool in removing tooth structure from the tooth to be treated in an occlusal direction down to a distance just above gingival margin 96 where tooth 90 meets gingiva 95 below the crown of the tooth. As demonstrated by FIG. 11, the pathway of dental tool 150 caused by contact of dental tool 150 with guide 110 is one that includes movement in a direction parallel to the longitudinal axis of cutting tool 155, along with and even simultaneously with movement in a direction perpendicular to the longitudinal axis of the cutting tool as in other systems, such as those described in the '726 Application, such that the cutting tool removed tooth structure from the tooth to be treated at different distances in an occlusal direction as the cutting tool traveled through the guide to prepare tooth 90. In this manner, in general, the present technology allows tooth structure to be removed close to the gingival margin with only a single guide or with fewer preparation guides than guides previously known to those skilled in the art.

In particular, dental tool 150 contacts tooth preparation guide 110 at spaced apart positions, e.g., at locations where opposing first flanges 152A, 152B and opposing second flanges 154A, 154B contact opposing guide channels 122A, 122B to allow three-dimensional movement in the form of a "roller coaster" as the spacing between the areas of contact between the dental tool and the guide provides a space for a portion of the guide to reside without contacting, and thus without interfering with, the dental tool. In this manner, dental tool 150 in combination with tooth preparation guide 110 is able to move vertically and horizontally along the path taken by the dental tool through the tooth preparation guide. In some arrangements, dental tool 150 in combination with another tooth preparation guide is able to move either one or both vertically and horizontally as well as to optionally tilt along the path taken by the dental through the tooth preparation guide. Through any one or any combination of such vertical, horizontal, and tilt movements, the cutting depth (i.e., the amount of tooth structure configured for removal from the working tooth or working teeth in a direction transverse to a longitudinal axis of cutting tool 155) and the cutting height (i.e., the amount of tooth structure configured for removal from the working tooth or working teeth in a direction along the longitudinal axis of cutting tool 155) may be altered along the path dental tool 150 travels through guide 110. In this manner, dental tool 150 may follow along the gum line of a patient, forming a smooth finish line for the patient, and thereby prepare the working tooth or teeth to receive an implant, e.g., a "margin" crown, that extends to the gum line of the patient. Further, dental tool 150 may be controlled within a tooth preparation guide to be more minimally invasive such that less tooth structure may be removed from a working tooth or working teeth using dental tool 150 in combination with a tooth preparation guide, such as tooth preparation guide 110, than prior tooth preparation systems. In prior systems, a plurality of tooth preparation guides are needed to achieve the same removal of tooth structure as may be accomplished using dental tool 150 and suitable tooth preparation guide for receiving the dental tool.

Figure 4:
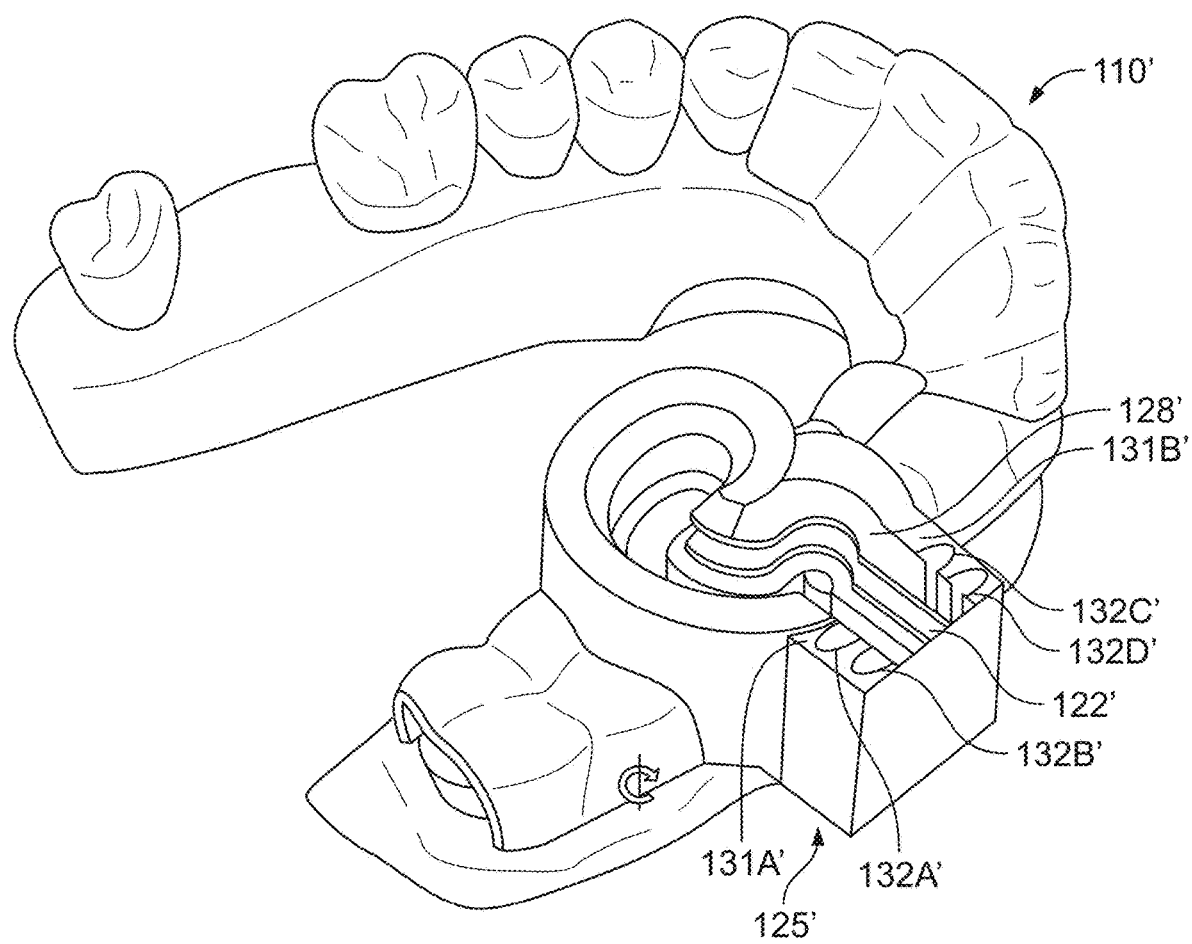
FIG. 4 is a perspective view of a tooth preparation guide in accordance with another embodiment.

Referring now to FIG. 4, tooth preparation guide 110' may be the same or substantially the same as tooth preparation guide 110 with the notable exception that insertion section 125 may be replaced by insertion section 125'. Insertion section 25' may be the same or substantially the same as insertion section 125 with the notable exceptions that insertion section 125' does not include entryway 132 and instead includes passageways 132A'-132D' for insertion of a dental tool such as dental tool 150 into guide 110'. In this manner, a tooth preparation system including tooth preparation guide 110' may be the same as tooth preparation system 100 with the exception of the differences between guide 110' and guide 110. As shown, passageways 132A'-132D' extend from surfaces 131A', 131B' to respective opposing guide channels 122' that are the same as opposing guide channels 122A, 122B with the exception of the interfaces of the guide channels with the passageways. As further shown, passageways 132A'-132D' further extend through opposing chamfered edges 128' that may be the same as opposing chamfered edges 128A, 128B with the exception of the interfaces of the chamfered edges with the passageways. With passageways 132A'-132D' configured as shown, first flange 152A of dental tool 150 may be received through passageway 132A', second flange 154A of dental tool 150 may be received through passageway 132B', first flange 152B of dental tool 150 may be received through passageway 132C', and second flange 154B of dental tool 150 may be received through passageway 132D' such that all of the flanges are then received into opposing guide channels 122'. Each of first and second connection bars 151, 153 of dental tool 150 may be received through opposing chamfered edges 128' such that the connection bars are then received into opposing flange openings 127' that may be the same as opposing flange openings 127A, 127B with the exception of the interfaces of the flange openings with respective passageways 132A'-132D'. In this manner, dental tool 150 may be received in guide 110' such that the contact of the dental tool with the guide guides the dental tool in the removal of tooth structure from the tooth to be treated in the same manner as guide 110 contacts the dental tool to guide the dental tool in the removal of tooth structure from the tooth to be treated.

Figure 5A:
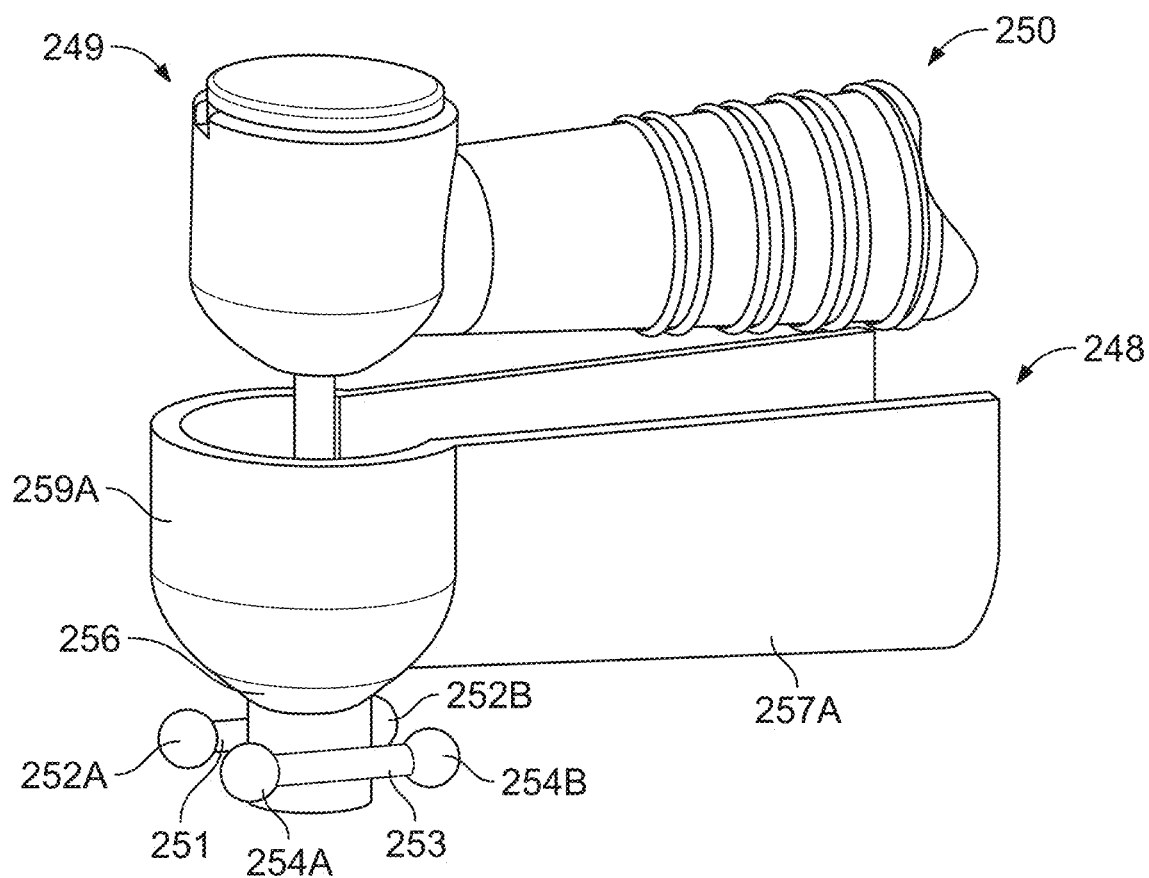
FIGS. 5A and 5B are perspective views of a dental tool, shown in pre-assembled and assembled states, respectively, in accordance with another embodiment.
Figure 5B:
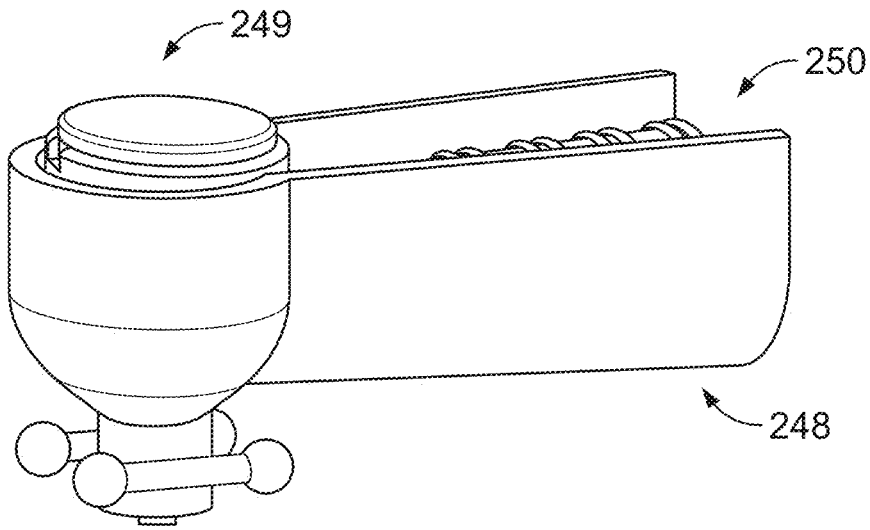

With reference now to FIGS. 5A and 5B, dental tool 250 takes substantially the same form as dental tool 150 but utilizing a two-piece assembly in which dental tool 250 includes dental handpiece 249, which as in the example shown may be in the form of a standard dental handpiece as known to those skilled in the art, and outer shell guide 248. Outer shell guide 248 includes handle shell 257A, main head shell 259A, guide head shell 256, first connection bar 251, opposing first flanges 252A, 252B, second connection bar 253, and second flanges 254A, 254B but excludes cutting tool 255 which is part of dental handpiece 249. Outer shell guide 248 generally may be made of a substantially rigid material such as but not limited to a metal, e.g., stainless steel or aluminum, or a plastic, e.g., polyethylene, polypropylene, acrylic, or acetal.

As shown, handle shell 257A, main head shell 259A, and guide head shell 256A of outer shell guide 248 form an open cover for wrapping around longitudinal axes defined by handle 257B, main head 259B, and guide head 258B of dental handpiece 249. In this manner, as shown by the contrast between FIGS. 5A and 5B, dental handpiece 249 is insertable into and removable from outer shell 248 in which cutting tool 255 extends through a bottom, i.e., an outermost, portion of guide head shell 256 when the dental handpiece is fully inserted into the outer shell guide and the cutting tool is pulled through the guide head shell when the dental handpiece is removed from the outer shell guide. First connection bar 251, opposing first flanges 252A, 252B, second connection bar 253, and second flanges 254A, 254B are in the same form and operate in the same manner as corresponding first connection bar 151, opposing first flanges 152A, 152B, second connection bar 153, and opposing second flanges 154A, 154B of dental tool 150.

Figure 6A:
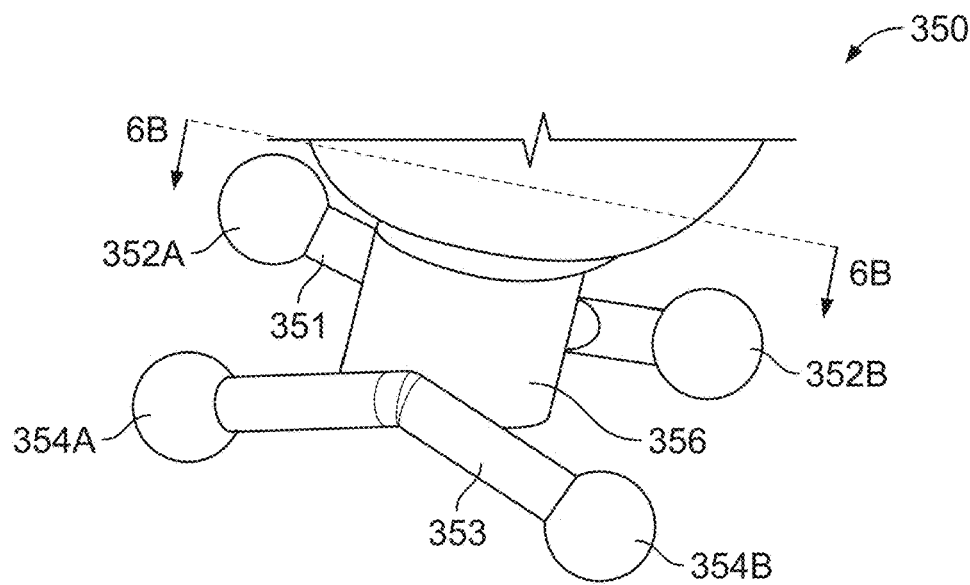
FIG. 6A is a partial perspective view of a dental tool in accordance with another embodiment.
Figure 6B:
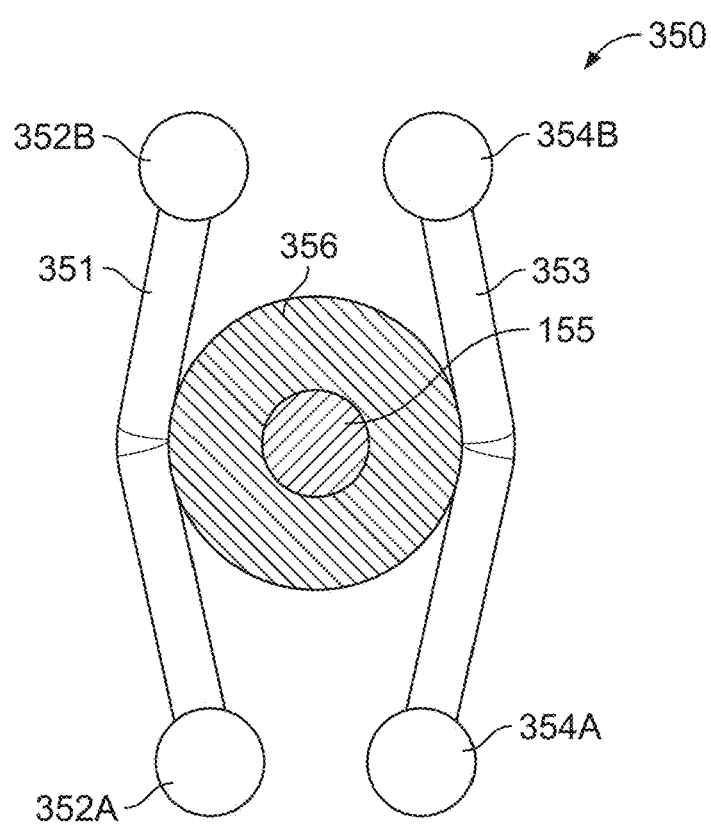
FIG. 6B is a cross-sectional plan view of the dental tool of FIG. 6A along lines 6B-6B.

Referring now to FIGS. 6A and 6B, dental tool 350 is the same or substantially the same as dental tool 150 with the exception that dental tool 350 includes guide head 356, first connection bar 351 extending from guide head 356, first flanges 352A, 352B attached to first connection bar 351 on opposing ends of the first connection bar, second connection bar 353, and second flanges 354A, 354B attached to second connection bar 353 on opposing ends of the second connection bar in place of corresponding first connection bar 151, opposing first flanges 152A, 152B, second connection bar 153, and opposing second flanges 154A, 154B of dental tool 150. Guide head 356, first connection bar 351, and second connection bar 353 are the same or substantially the same as corresponding guide head 156, first connection bar 151, and second connection bar 153 of dental tool 150 with the exception that first connection bar 351 and second connection bar 353 each include first and second portions extending from guide head 356 at an angle to each other and in transverse but non-perpendicular directions to directions that cutting tool 155 extends from guide head 356 as opposed to the single portion of first and second connection bars 151, 152 that extend from guide head 156 in directions parallel to each other and in directions orthogonal to the directions that cutting tool 155 extends.

As shown in FIG. 6A, first connection bar 351 is positioned higher along guide head 356 than second connection bar 353. As further shown, the first and second portions of first connection bar 351 are each linear and extend in a slightly upward direction, i.e., slightly in the direction opposite the direction that cutting tool 155 extends from guide head 356, and the first and second portions of second connection bar 353 extend in a slightly downward direction, i.e., slightly in the same direction to the direction that cutting tool 155 extends from the guide head. As shown in FIG. 6B, the first and second portions of first connection bar 351 also extend rearwardly and the first and second portions of second connection bar 353 also extend forwardly such that each of the first and second connection bars extend partially around a longitudinal axis defined by cutting tool 155. In this manner, first and second connection bars 351, 353 define opposing contact areas configured for contacting opposing points along a tooth preparation guide, e.g., tooth preparation guide 310 described further herein, thereby creating opposing forces acting against dental tool 350 such that first flanges 352A, 352B and second flanges 354A, 354B may glide smoothly along guide channels, such as upper and lower guide channels 322A, 322B, 322C, 322D of guide 310, in which the flanges are received.

Figure 6C:
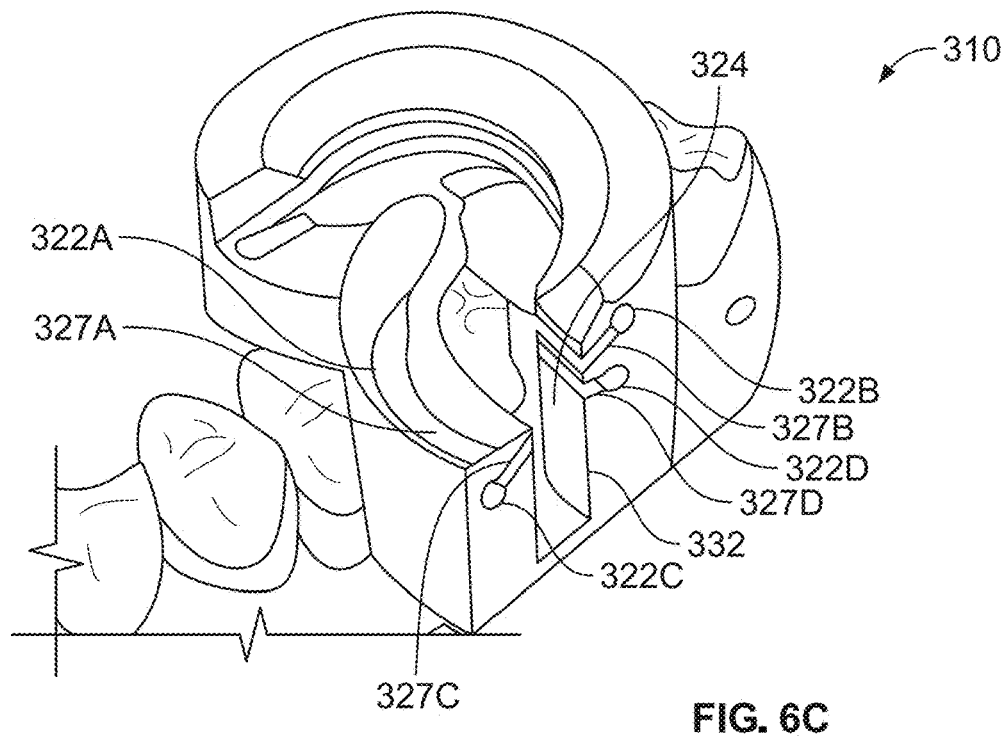
FIG. 6C is a partial cross-sectional perspective view of a tooth preparation guide in accordance with another embodiment.
Figure 6D:
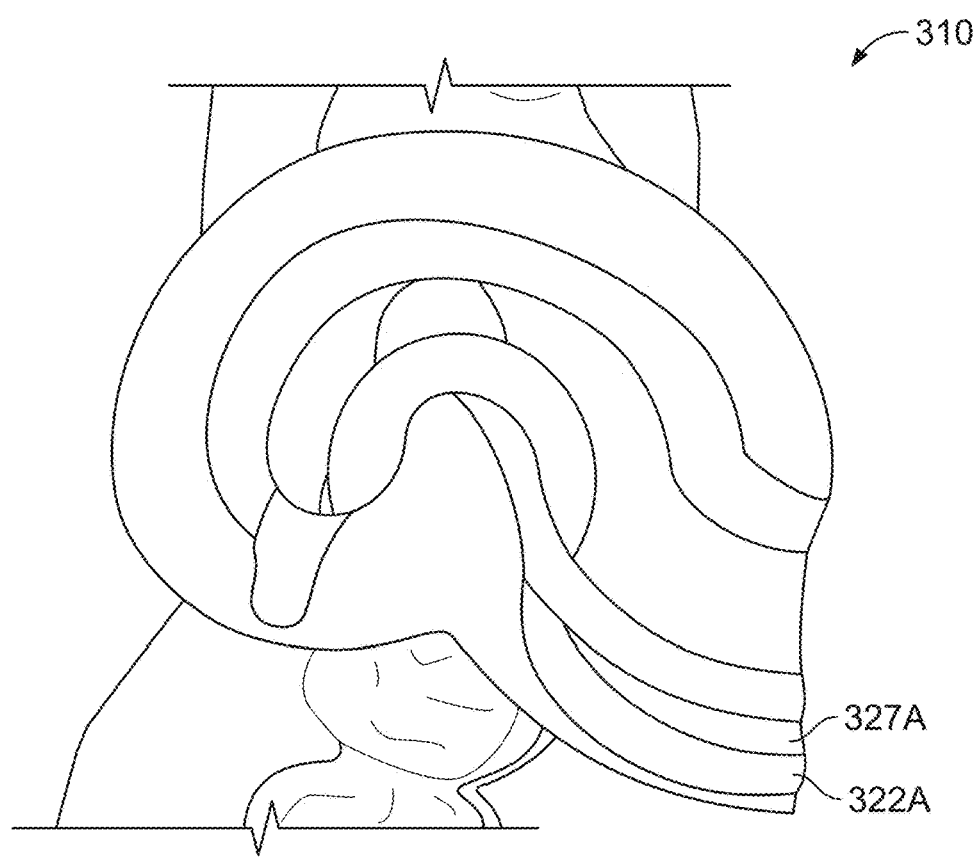
FIG. 6D is a partial cross-sectional plan view of the tooth preparation guide of FIG. 6C.

As shown in FIGS. 6C and 6D, tooth preparation guide 310 is similar to tooth preparation guide 110 with the notable exceptions that tooth preparation guide 310 includes opposing upper guide channels 322A, 322B and opposing lower guide channels 322C, 322D in place of opposing guide channels 122A, 122B, elongated opposing upper bar apertures or openings 327A, 327B and elongated opposing lower bar apertures or openings 327C, 327D in place of flange openings 127A, 127B, and head channel 324 in place of the combination of head channel 124 and tool channel 126. Like tooth preparation guide 110, tooth preparation guide 310 is configured for removing tooth structure to prepare a tooth to receive a dental crown, although tooth preparation guide 310 has a general curvature configured for limiting the movement of dental tool 350 to make an anterior cut of a tooth whereas tooth preparation guide 110 has a general curvature configured for limiting the movement of dental tool 150 to make a posterior cut of a tooth.

In this example, head channel 324 has a width sufficient to receive guide head 356 in which such width is constant along a length of the head channel to the bottom of entryway 332. As shown by FIG. 6C, four guide channels 322A-322D and four bar apertures 327A-327D (guide channel 322A and bar aperture 327A being shown in cross-section) collectively define an overall channel having a cross-section generally in the form of an "X" providing additional stability relative to tooth preparation guide 110, including anti-tilting, of a dental tool such as dental tool 350 inserted into tooth preparation guide 310 with first flanges 352A, 352B received in corresponding upper guide channels 322A, 322B and second flanges 354A, 354B received in corresponding lower guide channels 322C, 322D.

The "X" formation generally continues, with the exception of gaps and crossovers noted below, throughout the length of the overall guide channel defined by guide channels 322A-322D and bar apertures 327A-327D. However, to accommodate the different vertical locations of first flange 352A and second flange 354A relative to guide head 356 and the different vertical locations between first flange 352B and second flange 354B described previously herein, the distance between upper guide channel 322A and lower guide channel 322C as well as the distance between upper guide channel 322B and lower guide channel 322D fluctuates along the length of the overall guide channel defined by guide channels 322A-322D and bar apertures 327A-327D. As with tooth preparation system 100, the system of tooth preparation guide 310 and dental tool 350 provides a "roller coaster" effect, exhibiting three-dimensional movement in which the cutting depth and the cutting height is altered along the path dental tool 350 travels through guide 310.

In the example shown, guide channels 322A-322D include curves along their lengths, although in alternative arrangements, the guide channels may include linear portions, e.g., within the insertion section that initially receives dental tool 350. Additionally, in the example shown, gaps are provided in guide channels 322A-322D such that, along portions of the path traversed by dental tool 350 when the dental tool is moved along guide channels 322A-322D through tooth preparation guide 310, only one flange of flanges 252A, 252B, 254A, 254B may be within its corresponding gap and not within its corresponding guide channel (see, e.g., FIG. 7C). Along the path taken by dental tool 350 within tooth preparation guide 310, the particular flange of flanges 252A, 252B, 254A, 254B within its corresponding gap may change along the path. In the same manner that guide channels 122A, 122B criss-cross, i.e., cross over each other, guide channel 322A and guide channel 322B criss-cross and guide channel 322C and guide channel 322D criss-cross.

Still referring to FIGS. 6C and 6D, the curvature of the paths defined by guide channels 322A-322D and the close approximation in size and form between corresponding guide channels and flanges 252A, 252B, 254A, 254B received in the guide channels dictates that the distance between guide channel 322A and guide channel 322B and the distance between guide channel 322C and guide channel 322D fluctuates along the paths of the guide channels such that none of the guide channels are parallel.

To maintain opposing forces on first and second connection bars 351, 353 of dental tool 350 through contact of the tool with tooth preparation guide 310 along the tool path to be taken by dental tool 350 during movement of the tool through the guide, each flange of first flanges 352A, 352B and each flange of second flanges 354A, 354B take paths that are non-parallel to the paths of the other flanges 352A, 352B, 354A, 354B. In other words, flanges 352A, 352B, 354A, 354B follow four different paths along the tool path to be taken by dental tool 350 when the tool is moved through guide 310. In the arrangement of FIGS. 6A-6D, the directions being taken by flanges 352A, 352B, 354A, 354B at each of the points along the tool path to be taken by dental tool 350 when the tool is moved through guide 310 are different. The use of these differing paths to provide the opposing forces on first and second connection bars 351, 353 of dental tool 350 further aids in achieving stability of the dental tool and inhibiting or preventing tilting of the tool during movement of the tool through guide 310.

In other arrangements, at least portions of the paths followed by flanges of a dental tool within a tooth preparation guide may be in the same directions as portions of the paths followed by some or all of the other flanges of the flanges of such dental tool. In these alternative arrangements, such portions of the paths followed by the flanges may be parallel to corresponding portions of the paths followed by the other flanges of such dental tool.

In some arrangements, portions or all of either one or both of the set of bar apertures 327A-327D and head channel 324 may have a size and form closely approximating respective portions or all of respective first and second connection bars 351, 353 and guide head 356. In this manner, contact of bar apertures 327A-327D and head channel 324 with first and second connection bars 351, 353 and guide head 356, respectively, provides additional guidance, and in some arrangements inhibits or prevents tilting, of dental tool 350 by way of the tool path formed within tooth preparation guide 310 defined by guide channels 322A-322D and the one or both of the set of bar apertures 327A-327D and head channel 324 in such arrangements.

Figure 7:
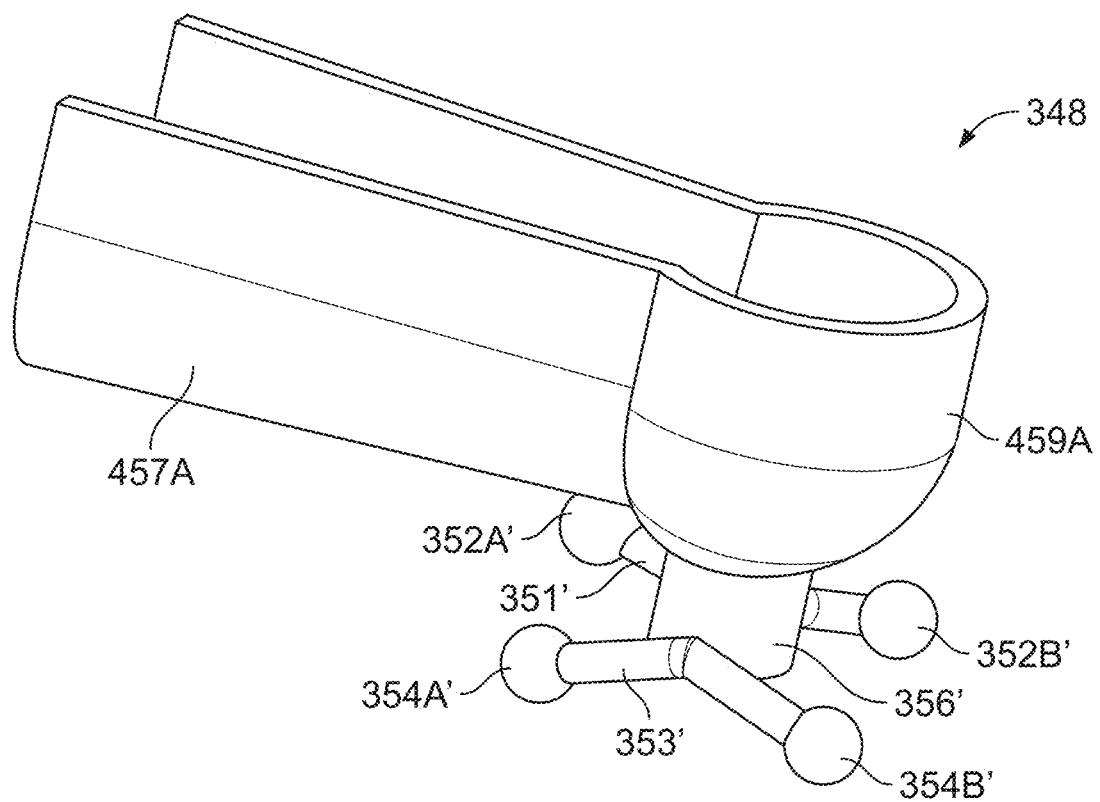
FIG. 7 is a perspective view of an outer shell guide in accordance with another embodiment.

As shown in FIG. 7, in some alternative arrangements, guide head 356', first connection bar 351', first flanges 352A', 352B', second connection bar 353', and second flanges 354A', 354B', which as shown are substantially in the same form as their counterparts of dental tool 350, form parts of outer shell guide 348. Outer shell guide 348, which operates in a manner and is made of materials that are the same or similar to outer shell guide 248, may be fitted to dental handpiece 249 to form a dental tool operable in the same manner as dental tool 350. Such an outer shell guide may be attachable to and removable from dental handpiece 249. In other alternative arrangements, the outer shell guide may be a component to be clipped onto rather than fitted around dental handpiece 249.

Figure 8A:
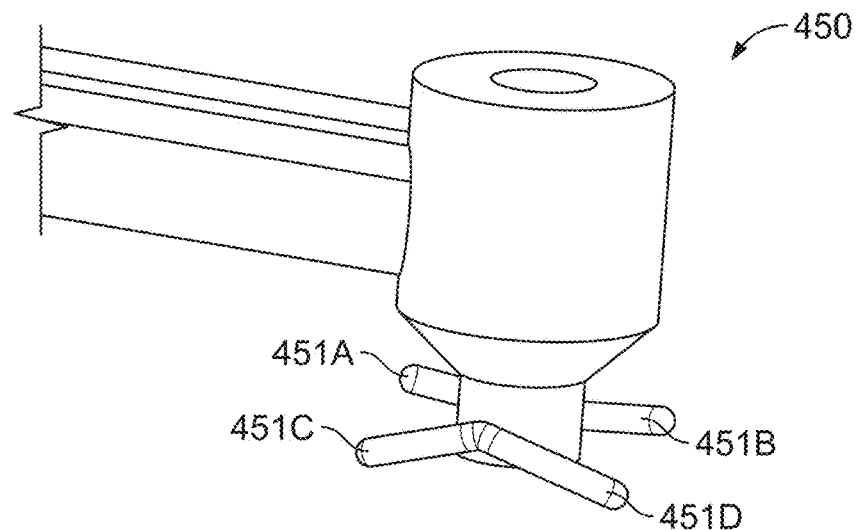
FIG. 8A is a perspective view of a portion of a dental tool in accordance with another embodiment.
Figure 8B:
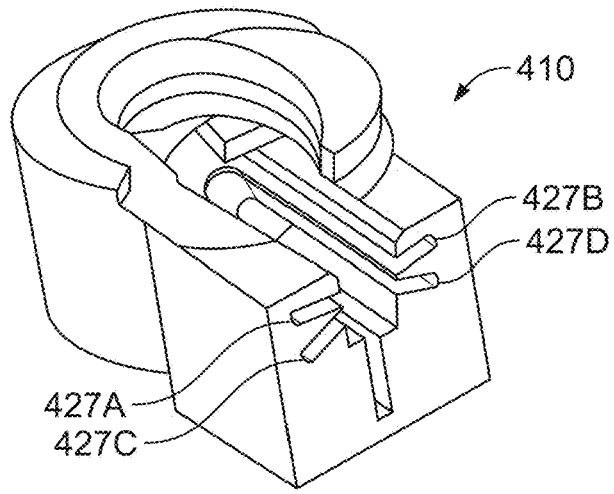
FIG. 8B is a perspective view of a tooth preparation guide in accordance with another embodiment.
Figure 8C:
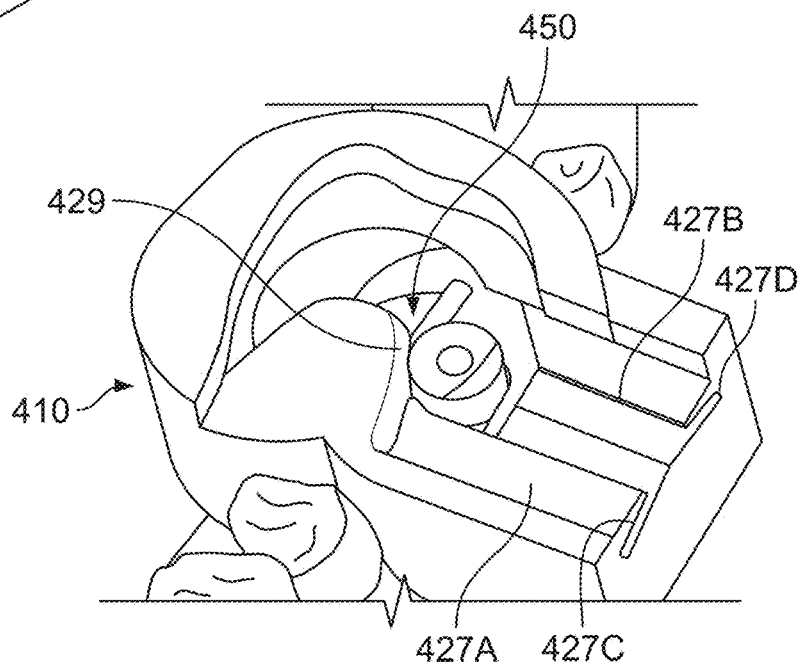
FIG. 8C is a perspective view of a tooth preparation system that includes the dental tool of FIG. 8A and the tooth preparation guide of FIG. 8B in accordance with an embodiment.

Referring now to FIGS. 8A and 8C, dental tool 450 is the same or substantially the same as dental tool 350 with the exception that dental tool 450 excludes flanges on the ends of first and second portions 451A, 451B of a first connection bar and on the ends of first and second portions 451C, 451D of a second connection bar. As best shown in FIG. 8A, first connection bar 451A, 451B is located at a higher position, i.e., closer to the guide head and handle of dental tool 450, than second connection bar 451C, 451D. As shown in related FIGS. 8B and 8C, tooth preparation guide 410 is the same or substantially the same as tooth preparation guide 310 with the notable exception that tooth preparation guide 410 includes elongated upper bar apertures 427A, 427B and elongated lower bar apertures 427C, 427D that are in substantially the same form as upper bar apertures 327A, 327B and lower bar apertures 327C, 327D and excludes guide channels in the form of guide channels 322A-322D. Bar apertures 427A-427D have a substantially equal diameter to corresponding first and second portions of connection bars 151, 153 such that the bar apertures contact the connection bars to limit the movement of dental tool 450 as the dental tool traverses the length of the bar apertures. In this manner, bar apertures 427A-427D serve a similar function to that served by guide channels such as guide channels 322A-322D described previously herein.

As further shown in FIG. 8C, tooth preparation guide 410 includes obliquely angled walls configured to contact connection bars 451, 453 of dental tool 450. For example, tooth preparation guide 410 includes wall 429 along bar aperture 427A configured to abut first portion 451A of the upper connection bar such that the first portion of the upper connection bar slides along the wall and is redirected by the wall.

It is to be understood that the first and second portions of each of the first and second connection bars of a dental tool may extend in any directions transverse to the directions that cutting tool 155 extend and that a tooth preparation guide for limiting the movement of such a dental tool may include an overall channel defined by any one or any combination of bar apertures and guide channels and having a cross section matching a projection of a guide head, one or more connection bars extending from guide head, and one or more flanges attached on the end or ends of any such connection bar onto a plane parallel to a plane passing between the first and second connection bars. Moreover, the location or locations of attachment of the connection bars to the guide head may be at different locations on the guide head in which multiple portions of the same connection bar (which may extend in different directions) may be attached to the guide head at the same location, such as in the example shown in FIGS. 6A and 6B. Any reasonable number of connection bars may be utilized so long as there is any one or any combination of corresponding bar apertures and guide channels in a corresponding tooth preparation guide.

In some alternative arrangements, first and second portions 451A, 451B of the first connection bar, the first and second portions 451C, 451D of the second connection bar, and a guide head to which the first and second connection bars are attached may be part of an outer shell guide, similar to outer shell guide 248, to be fitted to dental handpiece 249 to form a dental tool operable in the same manner as dental tool 450. Such an outer shell guide may be attachable to and removable from dental handpiece 249. In other alternative arrangements, the outer shell guide may be a component to be clipped onto rather than fitted around dental handpiece 249.

Figure 9A:
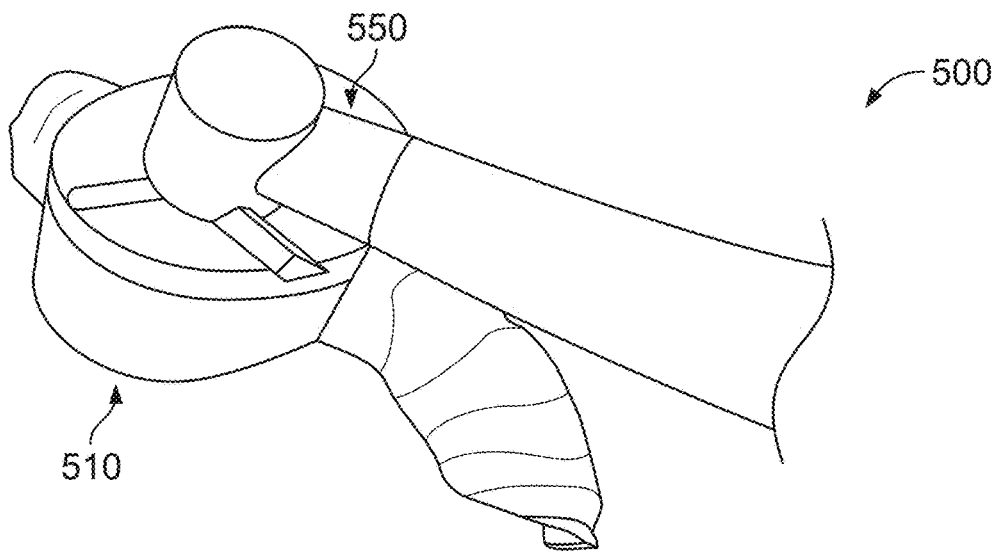
FIG. 9A is a perspective view of a tooth preparation system in accordance with another embodiment.
Figure 9B:
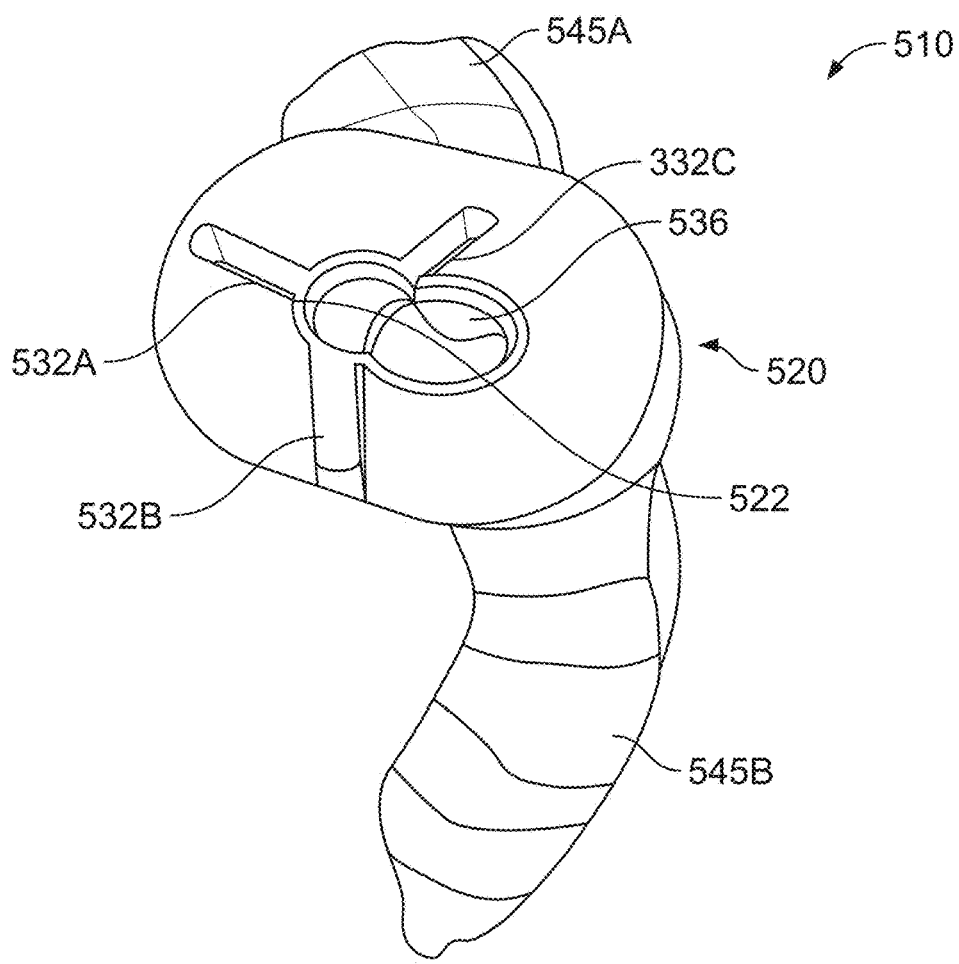
FIG. 9B is a perspective view of a tooth preparation guide of the tooth preparation system of FIG. 9A in accordance with another embodiment.

With reference to FIGS. 9A-9B, tooth preparation system 500 includes tooth preparation guide 510 and dental tool 550. Tooth preparation guide 510 may be configured for removing tooth structure from a first molar of a patient in which the guide includes main body 520, distal wrap 545A extending from a distal side of the main body, and mesial wrap 545B extending from a mesial side of the base, which, like guides 110, 110', 310, 410 may be prepared in the manner disclosed in the '726 Application. As shown, distal wrap 545A and mesial wrap 545B may be substantially similar to distal wrap 145A, 145B of guide 110 with the exception that wraps 545A, 545B may have a contour conforming to the teeth on which such wraps are to be placed.

Main body 520 is configured to receive a dental tool, such as but not limited to dental tool 550. In the example shown, main body 520 includes a plurality of slots 532A-532C, guide channel 522, and tool aperture 536 that extends through a thickness of the main body. A combination of the plurality of slots 532A-532C and tool aperture 536 define an entryway for receipt of a dental tool, such as dental tool 550, into guide channel 522. The plurality of slots 532A-532C may be configured to be slightly larger than bars of the dental tool, such as bars 551A-551C of dental tool 550. In this manner, bars of such dental tool may only be removed from main body 520 of guide 510 through the entryway defined by the plurality of slots 532A-532C and tool aperture 536 such that the bars remain in guide channel 522 when the bars are not in alignment with the plurality of slots 532A-532C. As such, the bars of the dental tool may be either one or both of rotated and slid within guide channel 522 as the configuration of the guide channel permits. Guide channel 522 may extend substantially through main body 520 in a direction transverse, and preferably perpendicular, to the direction of insertion of the dental tool which generally may be in a direction the longitudinal axis of cutting tool 155 of dental tool 550. Thus, as shown, guide channel 522 may be parallel or at least substantially parallel to the entryway defined by the plurality of slots 532A-532C and tool aperture 536. Guide channel 522 may be configured in the form of a variety of profiles such that the guide channel contacts a dental tool inserted into guide 510 to guide the dental tool in a predetermined path, which may be linear or curvilinear, such as those paths described with respect to system 100 to prepare one or more teeth to be treated to receive any one of various restorations including but not limited to a crown, a veneer, or a bridge. Guide channel 522 further may be configured to contact portions of the dental tool, e.g., bars 551A-551C of dental tool 550, such that the dental tool moves in directions parallel to the cutting tool, such as cutting tool 155 of dental tool 550, which may be in directions towards and away from the tooth to be treated as in the example shown. Like tool aperture 136, tool aperture 536 may provide an opening for exposing the tooth or teeth to be treated for removal of tooth structure from the tooth or teeth to be treated. With such configurations, dental tool 550 may be used to guide a cutting tool of a dental tool to remove structure from a tooth to be treated to form prepared tooth 90 as described previously herein with respect to FIG. 11.

Figure 10A:
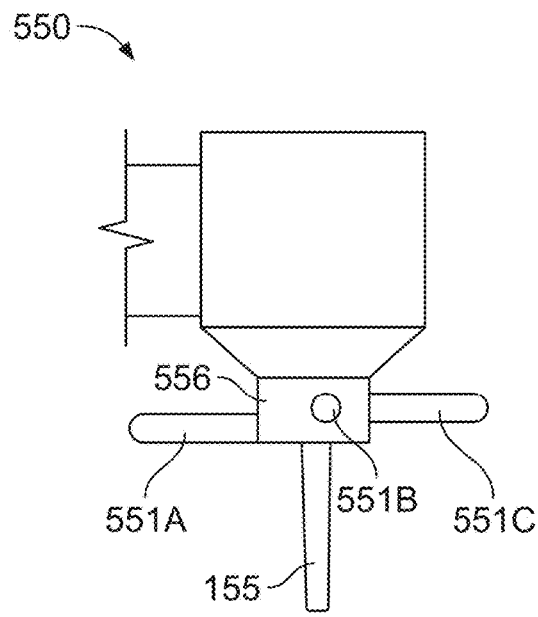
FIG. 10A is an elevation view of a dental tool of the tooth preparation system of FIG. 8A in accordance with another embodiment.
Figure 10B:
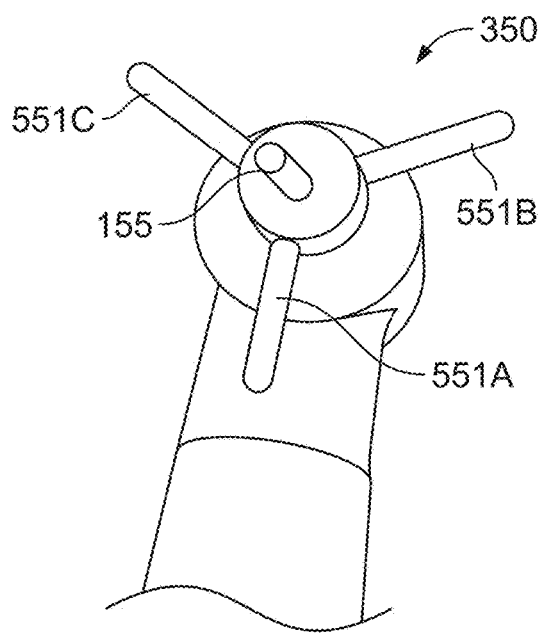
FIG. 10B is a perspective view of the dental tool shown in FIG. 9A.

Referring now to FIGS. 10A and 10B, dental tool 550 may be the same or at least substantially the same as dental tool 150 with the notable exceptions that dental tool 550 does not include first connection bar 151, opposing first flanges 152A, 152B, second connection bar 153, or second flanges 154A, 154B and instead includes the plurality of bars 551A-551C that extend from guide head 556. Respective longitudinal axes defined by each of the plurality of bars 551A-551C may be coplanar or at least substantially coplanar with one or more of the other of the plurality of bars in some arrangements. In the example shown, only bars 551B and 551C are coplanar as bar 551A does not lie in the same plane as bars 551B, 551C. The respective longitudinal axes defined by each of the plurality of bars 551A-551C may lie in a plane parallel to a plane in which one or more of the other of the plurality of bars lie. In the example shown, bar 551A lies in a plane parallel to a plane in which both of bars 551B and 551C lie. In this manner, dental tool 550 may be inhibited or prevented from tilting within planes perpendicular to such parallel planes or otherwise stabilized when the dental tool is inserted into main body 520 of dental preparation guide 510. As shown and in correspondence with the plurality of slots 532A-532C of main body 520 of guide 510, each of the plurality of bars 551A-551C may be spaced apart circumferentially at equivalent angles from each other. In this manner, each of the bars 551A-551C may contact walls of main body 520 defining guide channel 522 such that the guide channel limits the three-dimensional movement of dental tool 550. As in the example shown, bars 551A-551C may extend from guide head 556 such that a first plane through both the longitudinal axis defined by any bar of bars 551A-551C and through the longitudinal axis defined by cutting tool 155 may intersect with a second plane through the longitudinal axis defined by another bar of bars 551A-551C and through the longitudinal axis defined by the cutting tool. In certain alternative arrangements, a dental tool similar to dental tool 550 may include only one bar, only two bars which in some such arrangements may define coplanar longitudinal axes, or greater than three bars which in some such arrangements may define coplanar longitudinal axes.

In some alternative arrangements, the plurality of bars 551A-551C and a guide head to which the plurality of bars are attached may be part of an outer shell guide, similar to outer shell guide 248, to be fitted to dental handpiece 249 to form a dental tool operable in the same manner as dental tool 550. Such an outer shell guide may be attachable to and removable from dental handpiece 249. In other alternative arrangements, the outer shell guide may be a component to be clipped onto rather than fitted around dental handpiece 249.

Figure 12:
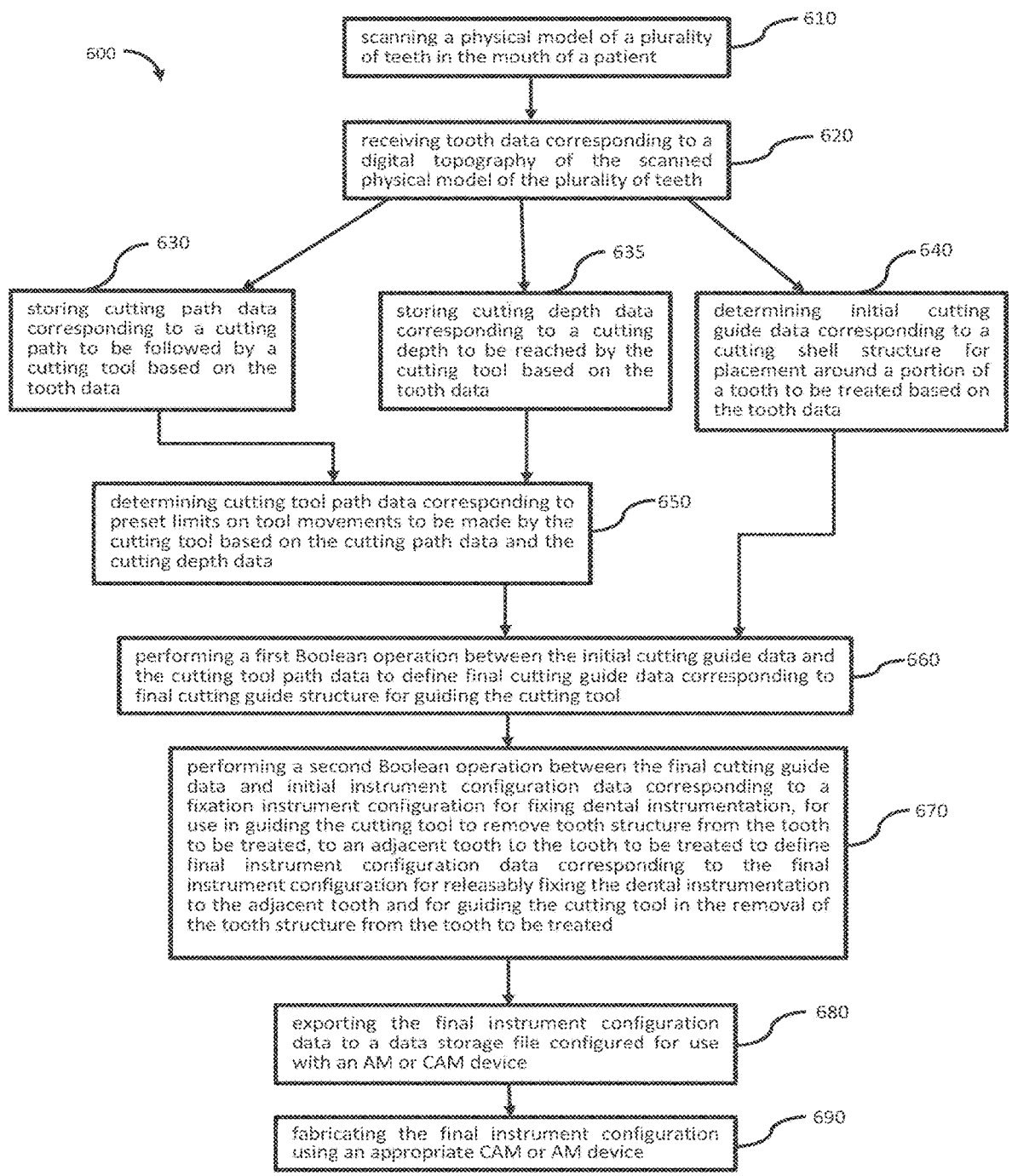
FIG. 12 is a process flow diagram of a process for preparing a dental instrument in accordance with an embodiment.

As shown in FIG. 12, process 600 prepares a working tooth or working teeth to receive a restoration, in a similar manner to the process described in the '726 Application. At block 610, a physical model of a plurality of teeth in the mouth of a patient is scanned by a suitable scanner. At block 620 and following the step at block 610, tooth data corresponding to digital topography of the scanned physical model of the plurality of teeth is received by one or more processors of a second client computer which may receive the tooth data from a first client computer in which the client computers may be remote from each other. At block 630 and following the step at block 620, cutting path data corresponding to a cutting path to be followed by a dental cutting tool based on the tooth data may be stored by one or more processors of the second client computer. At block 635 and following the step at block 620, cutting depth data corresponding to a cutting depth to be reached by the cutting tool based on the tooth data is stored by one or more processors of the second client computer. The steps at blocks 630 and 635 may be performed in any order, including simultaneously. At block 640 and following the step at block 620, initial cutting guide data corresponding to a cutting guide shell structure for placement around a portion of a tooth to be treated and based on the tooth data is determined by one or more processors of the second client computer. At block 650 and following the steps at blocks 630 and 635, cutting tool path data corresponding to preset limits on tool movements to be made by the cutting tool is determined by one or more processors of the second client computer based on the cutting path data and the cutting depth data. At block 660 and following the steps at blocks 640 and 650, a first Boolean operation between the initial cutting guide data and the cutting tool path data is performed by one or more processors of the second client computer to define final cutting guide data corresponding to final cutting guide structure for guiding the cutting tool. At block 670 and following the step at block 660, a second Boolean operation is performed between the final cutting guide data and initial instrument configuration data corresponding to a fixation instrument configuration for fixing dental instrumentation, which is for use in guarding the cutting tool to remove tooth structure from the tooth to be treated, to an adjacent tooth to the tooth to be treated. In this manner, final instrument configuration data corresponding to the final instrument configuration for releasably fixing the dental instrumentation to the adjacent tooth and for contacting the cutting tool to guide the cutting tool in the removal of the tooth structure for the tooth to be treated is defined. At block 680 and following the step at block 670, the final instrument configuration data is exported to a data storage file configured for use with an additive manufacturing (AM) or computer-aided manufacturing (CAM) device. At block 690 and following the step at block 680, the final instrument configuration is fabricated using an appropriate CAM or AM device. The final instrument configuration may be but is not limited to being in the form of tooth preparation guides 110, 110', 310, 410, 510.

It is to be further understood that the disclosure set forth herein includes any possible combinations of the particular features set forth above, whether specifically disclosed herein or not. For example, where a particular feature is disclosed in the context of a particular aspect, arrangement, configuration, or embodiment, that feature can also be used, to the extent possible, in combination with and/or in the context of other particular aspects, arrangements, configurations, and embodiments of the technology, and in the technology generally.

Furthermore, although the technology herein has been described with reference to particular features, it is to be understood that these features are merely illustrative of the principles and applications of the present technology. It is therefore to be understood that numerous modifications, including changes in the sizes of the various features described herein, may be made to the illustrative embodiments and that other arrangements may be devised without departing from the spirit and scope of the present technology. In this regard, the present technology encompasses numerous additional features in addition to those specific features set forth in the claims below. Moreover, the foregoing disclosure should be taken by way of illustration rather than by way of limitation as the present technology is defined by the claims set forth below.

The invention claimed is:

1. A dental guide device for contacting a dental tool to limit the movement of the dental tool in the removal of a predetermined portion of tooth structure from a tooth to be treated in the mouth of a patient, the dental guide device comprising:
an inner surface configured for attachment to a first tooth such that the dental guide device is releasably fixable to the first tooth; and
a main body attached to the inner surface and comprising:
a first guide channel extending at least partially through the main body and defining a channel longitudinal axis, the first guide channel being configured for contacting a first flange of the dental tool extending from a shaft of the dental tool to limit a movement of the dental tool and defining a first channel diameter in a first direction perpendicular to one or more directions the channel longitudinal axis extends;
an aperture extending through the main body and configured to expose at least the predetermined portion of the tooth to be treated; and
a first opening extending between the first guide channel and the aperture, wherein the first opening has a first opening diameter that is less than the first channel diameter and the aperture extends beyond the first opening in the first direction.

2. The device of claim 1, wherein the channel longitudinal axis is curvilinear or linear.

3. The device of claim 1, wherein a cross-section of the first guide channel defines an oval or a polygon.

4. The device of claim 1, wherein the first guide channel extends through a sidewall of the main body to define an entryway configured for receipt of the dental tool into the first guide channel in a direction parallel to a direction the channel longitudinal axis extends through the entryway.

5. The device of claim 1, further comprising a passageway intersecting the first guide channel and extending through a sidewall of the main body in a direction transverse to a direction the channel longitudinal axis extends at the intersection between the passageway and the first guide channel, the passageway being configured for receipt of the flange of the dental tool through the passageway and into the first guide channel.

6. The device of claim 1, wherein the main body further comprises:
   a second guide channel extending at least partially through the main body, the second guide channel being configured for contacting a second flange of the dental tool extending from the shaft of the dental tool to limit the movement of the dental tool and defining a second channel diameter in the first direction; and
   a second opening extending between the second guide channel and the aperture, the second opening having a second opening diameter that is less than the second channel diameter.

7. The device of claim 6, wherein the first and the second guide channels intersect such that the second guide channel further defines the channel longitudinal axis.

8. The device of claim 6, wherein the first and the second guide channels do not intersect.

9. The device of claim 6, wherein the first and the second guide channels extend through a sidewall of the main body to define an entryway configured for receipt of the dental tool into the first and the second guide channels.

10. The device of claim 6, further comprising first and second passageways intersecting the first and the second guide channels, respectively, and extending through a sidewall of the main body in a direction transverse to the direction the channel longitudinal axis extends at the intersection between the first passageway and the first guide channel, wherein the first and the second passageways are configured for receipt of opposing first and second flanges of the dental tool through the first and the second passageways and into the first and the second guide channels, respectively.

11. The device of claim 10, further comprising third and fourth passageways extending through the sidewall of the main body in the direction transverse to the direction the channel longitudinal axis extends at the intersection between the first passageway and the first guide channel and intersecting the first and the second guide channels at locations spaced apart from locations at which the first and the second passageways intersect the first and the second guide channels, respectively, wherein the third and the fourth passageways are configured for receipt of third and fourth flanges of the dental tool through the third and the fourth passageways and into the first and the second guide channels, respectively.

12. The device of claim 1, wherein a longitudinal axis defined by the first opening within a cross-section of the device extends at an oblique angle to a longitudinal axis defined by the aperture through the cross-section of the device.

13. A tooth preparation system for the removal of a predetermined portion of tooth structure from a tooth to be treated in the mouth of a patient to prepare the tooth to be treated for the placement of a restoration on the tooth to be treated, the system comprising:
   a dental tool comprising:
      a handpiece;
      opposing first and second flanges attached to the handpiece; and
      a cutting tool attached to the handpiece for removal of tooth structure, the cutting tool defining a central tool axis extending in a direction transverse to a direction each of the first and the second flanges extend; and
   the dental guide device of claim 9, wherein the first and the second guide channels include a curved section curving in a plane orthogonal to the central tool axis such that when the dental guide device is attached to the first tooth and the first and the second flanges of the dental tool are in contact with the first and the second guide channels, respectively, the first and the second guide channels limit the movement of the dental tool such that tooth structure is removable by the dental tool from any two sides of the tooth to be treated selected from the group consisting of the buccal, lingual, mesial, distal, and occlusal sides of the tooth to be treated.

\* \* \* \* \*